US011596606B2

(12) United States Patent
Emerson et al.

(10) Patent No.: US 11,596,606 B2
(45) Date of Patent: Mar. 7, 2023

(54) ACTIVATED CANNABINOID CONTROLLED RELEASE COMPOUND TABLET AND METHOD OF FORMING THE SAME

(71) Applicant: Metta Medical Inc., San Francisco, CA (US)

(72) Inventors: Christopher R. Emerson, San Francisco, CA (US); Christopher M. Antapli, San Francisco, CA (US); Flip Senn, Daly City, CA (US)

(73) Assignee: METTA MEDICAL INC, San Francisco, CA (US)

( * ) Notice: Subject to any disclaimer, the term of this patent is extended or adjusted under 35 U.S.C. 154(b) by 0 days.

(21) Appl. No.: 15/929,953

(22) Filed: May 29, 2020

(65) Prior Publication Data

US 2020/0375907 A1 Dec. 3, 2020

Related U.S. Application Data

(60) Provisional application No. 62/854,925, filed on May 30, 2019.

(51) Int. Cl.
*A61K 9/20* (2006.01)
*B82Y 40/00* (2011.01)
*B82Y 5/00* (2011.01)

(52) U.S. Cl.
CPC .......... *A61K 9/2095* (2013.01); *A61K 9/2009* (2013.01); *A61K 9/2013* (2013.01); *A61K 9/2054* (2013.01); *B82Y 5/00* (2013.01); *B82Y 40/00* (2013.01)

(58) Field of Classification Search
CPC .. A61K 9/2095; A61K 9/2009; A61K 9/2013; A61K 9/2054; B82Y 5/00; B82Y 40/00
See application file for complete search history.

(56) References Cited

U.S. PATENT DOCUMENTS

| | | | |
|---|---|---|---|
| 10,206,888 B2 | 2/2019 | Vu et al. | |
| 10,238,745 B2 | 3/2019 | Finley et al. | |
| 10,245,237 B2 | 4/2019 | De Vries et al. | |
| 2003/0229027 A1 | 12/2003 | Eissens et al. | |
| 2013/0281523 A1 | 10/2013 | Letendre et al. | |
| 2016/0361261 A1* | 12/2016 | Carpanzano | A61K 9/2054 |
| 2018/0263913 A1 | 9/2018 | Lefler et al. | |

(Continued)

FOREIGN PATENT DOCUMENTS

WO 2020222029 A1 11/2020

OTHER PUBLICATIONS

Williams, "Terpene Profile: Linalool", May 9, 2018, retrieved from https://monq.com/eo/terpenes/linalool on Oct. 30, 2020. (Year: 2018).*

(Continued)

*Primary Examiner* — Jianfeng Song
(74) *Attorney, Agent, or Firm* — Boisbrun Hofman, PLLC

(57) ABSTRACT

An activated cannabinoid controlled release compound tablet and method of forming the same. In one embodiment, the tablet includes a cannabinoid and a hosting compound mixed with the cannabinoid to form a cannabinoid controlled release compound. The tablet may also include a surfactant mixed with the cannabinoid controlled release compound to form an activated cannabinoid controlled release compound.

12 Claims, 28 Drawing Sheets

(56) References Cited

U.S. PATENT DOCUMENTS

| | | |
|---|---|---|
| 2018/0325861 A1 | 11/2018 | Domb et al. |
| 2018/0344641 A1 | 12/2018 | Brinker et al. |
| 2020/0215024 A1* | 7/2020 | Berman ................ A61K 36/82 |
| 2020/0345684 A1* | 11/2020 | Vialpando .............. A61K 9/145 |

OTHER PUBLICATIONS

Gumaste, Suhas G., et al., "Development of Solid SEDDS, IV: Effect of Adsorbed Lipid and Surfactant on Tableting Properties and Surface Structure of Different Silicates", p. 3170 to 3185, Published Jun. 26, 2013.

Nagabandi, Vijay kumar, et al., "Silica-Lipid Hybrid Microparticles for Improved Bioavailability of Bcs Class IV Drug", American Journal of Advanced Drug Delivery (www.ajadd.co.uk), 18 pages, Nov. 26, 2013.

Qiu, Yihong, et al., "Developing Solid Oral Dosage Forms", Pharmaceutical Theory & Practice, p. 749 to 750, Copyright Elsevier 2017, 2020.

Razzak, Md. Shaikhul Millat Ibn et al., "Impact of Sodium Lauryl Sulphate on the Release of Carbamazepine from Methocel K15M CR based Matrix Tablets", Bangladesh Pharmaceutical Journal 15(1): 79-82, 2012.

Xie, Junran et al., "Mesoporous Silica Particles as a Multifunctional Delivery System for Pain Relief in Experimental Neuropathy", Advanced Healthcare Materials, www.advhealthmat.de; wileyonlinelibrary.com , p. 1213-1221, 2016.

\* cited by examiner

ACTIVATED CANNABINOID CONTROLLED RELEASE COMPOUND TABLET AND METHOD OF FORMING THE SAME

TECHNICAL FIELD

The present disclosure is directed, in general, to the field of cannabis active compound formulation and, more particularly, to an activated cannabinoid controlled release compound tablet and method of forming the same.

BACKGROUND

Various cannabinoids are often purified or otherwise isolated from a cannabis plant, particularly from its leaves, to produce a material with certain desired pharmacological properties. An objective is to produce a readily consumable tablet that retains the desired pharmacological properties. A challenge occurs because the cannabinoids in a cannabis plant generally have different isoforms, not all of which are amenable for easy formation into a tablet. What is lacking in the art is a process that enables a combination of a suite of different cannabinoids, from granular to amorphous solids, to produce a free-flowing powder that can be readily formed into a tablet.

The result at the present time is reliance on directly utilizing the leaves of a cannabis plant, which involves extraction or consumption of an oil with an uncontrolled level of an active ingredient that deteriorates over time, and which leaves an unpleasant aftertaste in the mouth of a user. Accordingly, what is needed in the art is a system and method for producing a tablet with an identified quantity of an active cannabinoid ingredient that can be consumed by a user, with a predictable pharmaceutical result, and that retains its pharmacological properties over a period of time.

SUMMARY

These and other problems are generally solved or circumvented, and technical advantages are generally achieved, by advantageous embodiments of the present disclosure for an activated cannabinoid controlled release compound tablet (also referred to as a "tablet") and method of forming the same. In one embodiment, the tablet includes a cannabinoid and a hosting compound mixed with the cannabinoid to form a cannabinoid controlled release compound. The tablet may also include a surfactant mixed with the cannabinoid controlled release compound to form an activated cannabinoid controlled release compound.

The foregoing has outlined rather broadly the features and technical advantages of the present disclosure in order that the detailed description of the disclosure that follows may be better understood. Additional features and advantages of the disclosure will be described hereinafter, which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

For a more complete understanding of the present disclosure, reference is now made to the following descriptions taken in conjunction with the accompanying drawings, in which.

Corresponding numerals and symbols in the different figures generally refer to corresponding parts unless otherwise indicated, and may not be redescribed in the interest of brevity after the first instance. The FIGUREs are drawn to illustrate the relevant aspects of exemplary embodiments.

DETAILED DESCRIPTION

The making and using of the present exemplary embodiments are discussed in detail below. It should be appreciated, however, that the embodiments provide many applicable inventive concepts that can be embodied in a wide variety of specific contexts. The specific embodiments discussed are merely illustrative of specific ways to make and use a tablet with a known quantity of an active cannabinoid ingredient. While the principles will be described in the environment of producing a tablet with an identified quantity of a cannabinoid active pharmaceutical ingredient ("cAPI"), any composition or form factor with an identified quantity of like ingredients is well within the broad scope of the present disclosure.

Figure 1A:
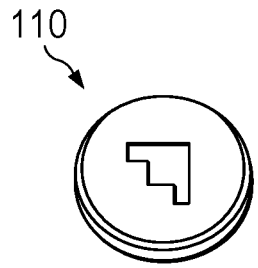
FIGS. 1A, 1B and 1C illustrate views of an embodiment of a cannabinoid tablet.
Figure 1B:
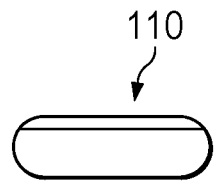
Figure 1C:
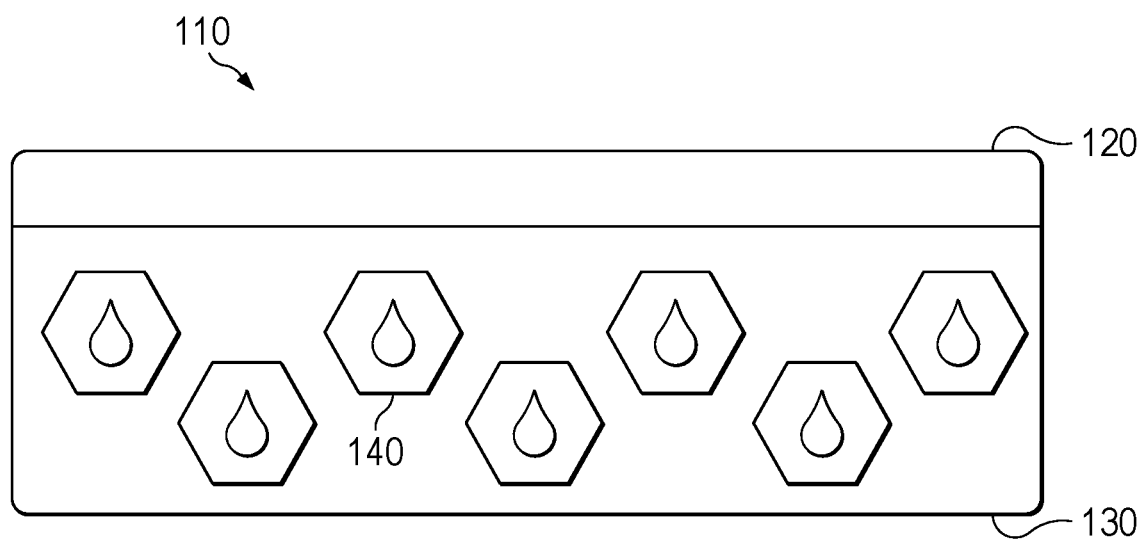

Turning now to FIGS. 1A, 1B and 1C, illustrated are views of an embodiment of a cannabinoid tablet 110. FIG. 1A illustrates a top view of the cannabinoid tablet 110, which is rotated along an axis to illustrate a side view of the cannabinoid tablet 110 in FIG. 1B.

FIG. 1C illustrates a cross sectional view of the cannabinoid tablet 110 including an upper surface 120 and lower surface 130. While the details will follow, the cannabinoid tablet 110 includes activated cannabinoid controlled release compound infused, for instance, with a terpenoid (generally designated 140).

Figure 2:
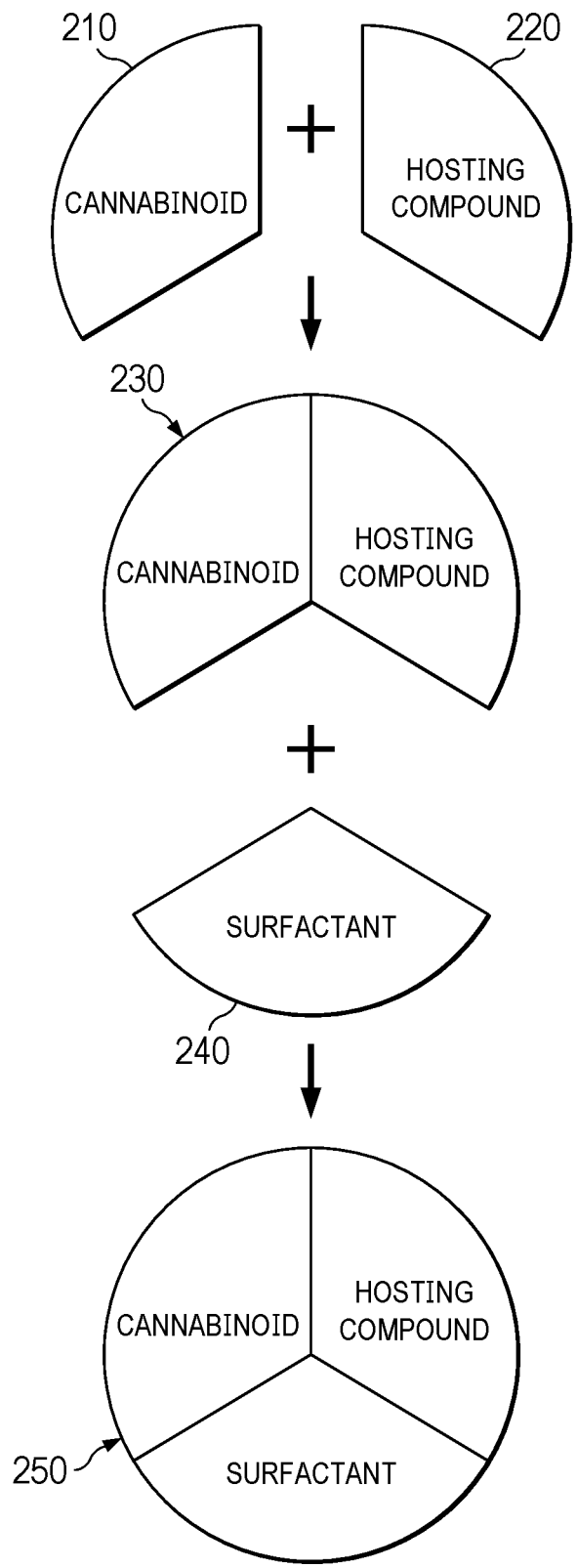
FIG. 2 illustrates a view of an embodiment of an activated cannabinoid controlled release compound.

Turning now to FIG. 2, illustrated is a view of an embodiment of an activated cannabinoid controlled release compound. A cannabinoid 210 is combined with a hosting compound 220. The hosting compound 220 may be any of various topology and material structure. The hosting compound 220 may be a manufactured templated material or a self-assembled material. Combining the cannabinoid 210 with the hosting compound 220 forms a cannabinoid controlled release compound 230. Although the cannabinoid controlled release compound 230 is an effective cannabinoid delivery compound, the addition of a surfactant 240 helps to increase bioavailability. Therefore, the surfactant 240 is combined with and integrated with the cannabinoid controlled release compound 230 to form the activated cannabinoid controlled release compound 250. Any addition order of these three components will work to achieve a desired version of the activated cannabinoid controlled release compound 250. It has been found, however, that the order of operation described, vide supra, provides enhanced results.

Figure 3:
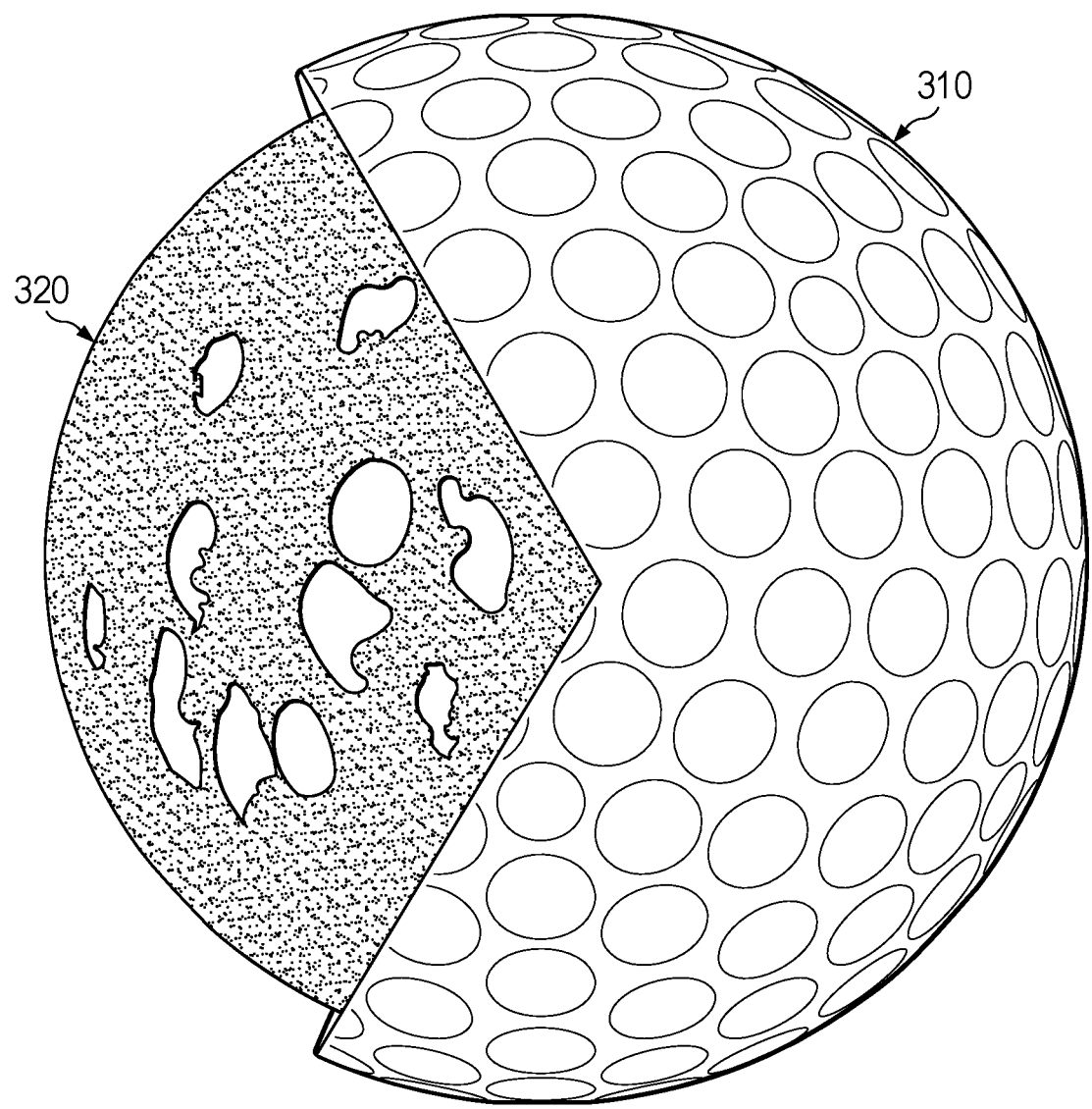
FIGS. 3 and 4 illustrate views of embodiments of a cannabinoid controlled release compound.

Turning now to FIG. 3, illustrated is a view of an embodiment of a cannabinoid controlled release compound. This representation is indicative of a mesoporous type compound. Although a mesoporous compound is formed with multiple layers with varying function, it is easier to understand the compound by conceptualizing that there are two layers. An exterior hosting layer 310 is typically produced by an adhesive process. Adhesion of cannabinoid on the exterior hosting layer 310 facilitates fast release of the cannabinoid. The second layer is an internal layer 320 that is typically defined through absorption process. An intent of forming this type of compound is to leverage these various properties. The cannabinoid will adhere to the exterior hosting layer 310. The cannabinoid functions as the absorbate while the material functions as the absorbent. The cannabinoid is absorbed into the hosting areas within the internal layer 320. These two different types of processes facilitate the controlled release character of the activated cannabinoid controlled release compound.

Figure 4:
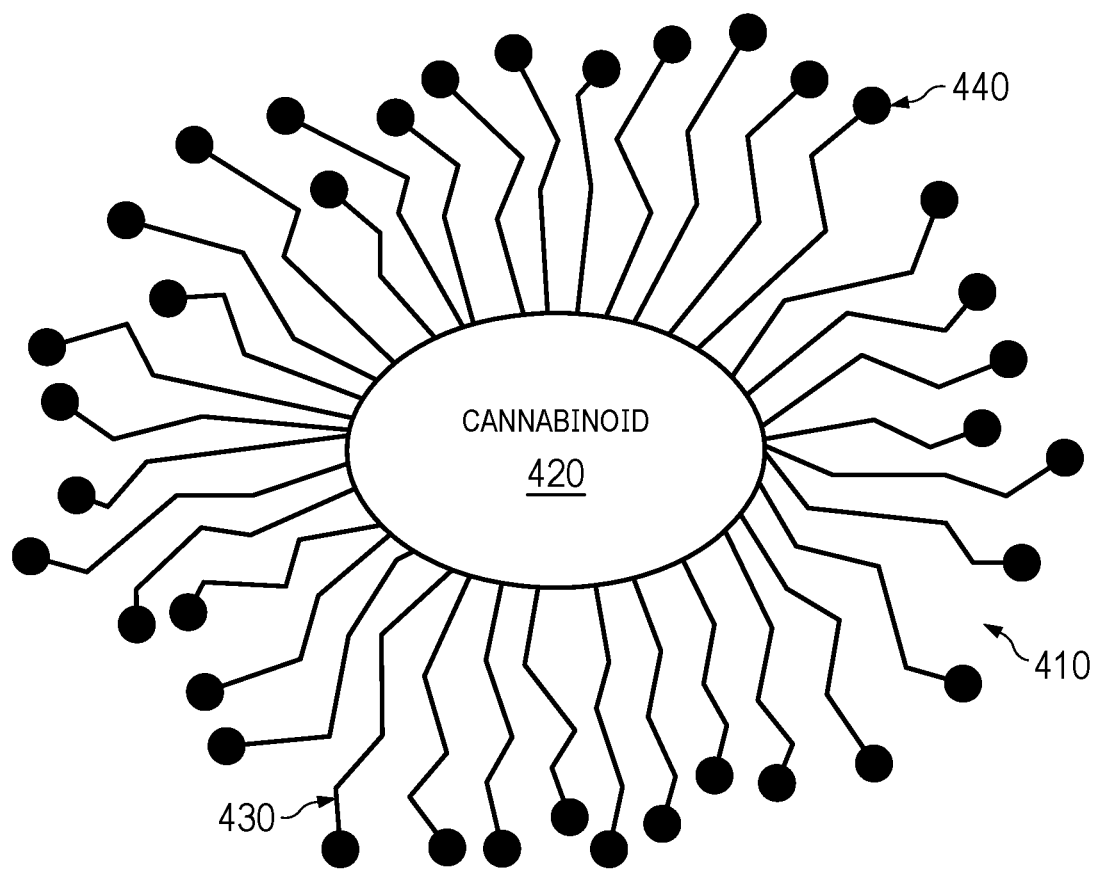

Turning now to FIG. 4, illustrated is view of an embodiment a cannabinoid controlled release compound (e.g., a nano-particle cannabinoid controlled release compound). This representation is indicative of a templated, self-assembled type compound (a nano-particle). There are many ways this type of hosting compound can be made. For general descriptive purposes, the activated cannabinoid controlled release compound may include an exterior hosting layer 410, which is typically defined by an adhesive process. Additionally, the activated cannabinoid controlled release compound includes an internal layer 420 (e.g., an internal cannabinoid hosting layer), an amphoteric component tail 430, and an amphoteric component head 440.

Figure 5:
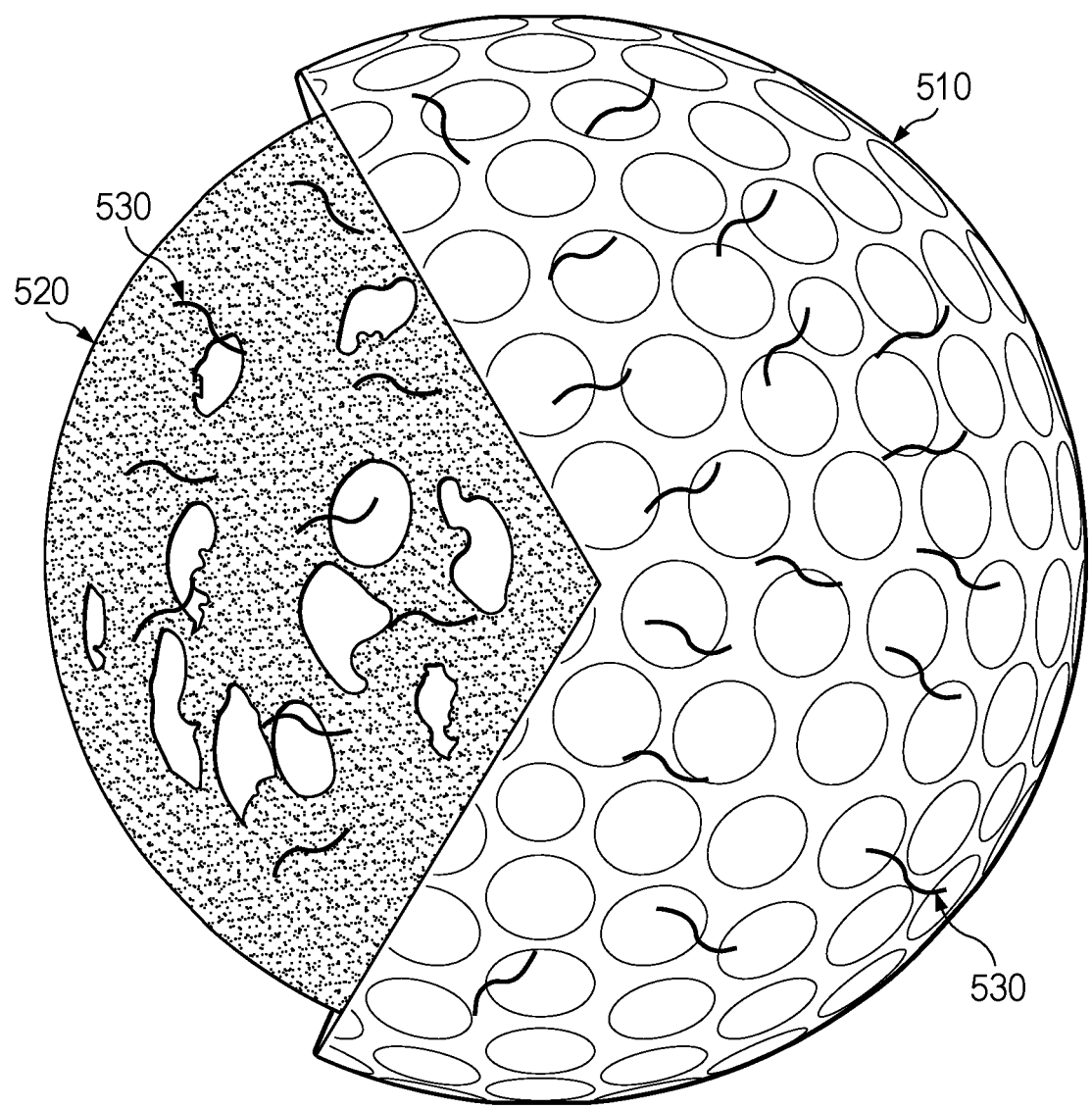
FIGS. 5 and 6 illustrate views of embodiments of an activated cannabinoid controlled release compound.

Turning now to FIG. 5, illustrative is a view of an embodiment of an activated cannabinoid controlled release compound. Analogous to FIG. 3 introduced above, an exterior hosting layer 510 is typically produced by an adhesive process. Adhesion of cannabinoid on the exterior hosting layer 510 facilitates fast release of the cannabinoid. The second layer is an internal layer 520 that is typically defined through absorption process. A surfactant 530 is added to form the activated cannabinoid controlled release compound (e.g., a mesoporous activated cannabinoid controlled release compound) and to facilitate an in situ extraction process of the absorbed cannabinoid.

Figure 6:
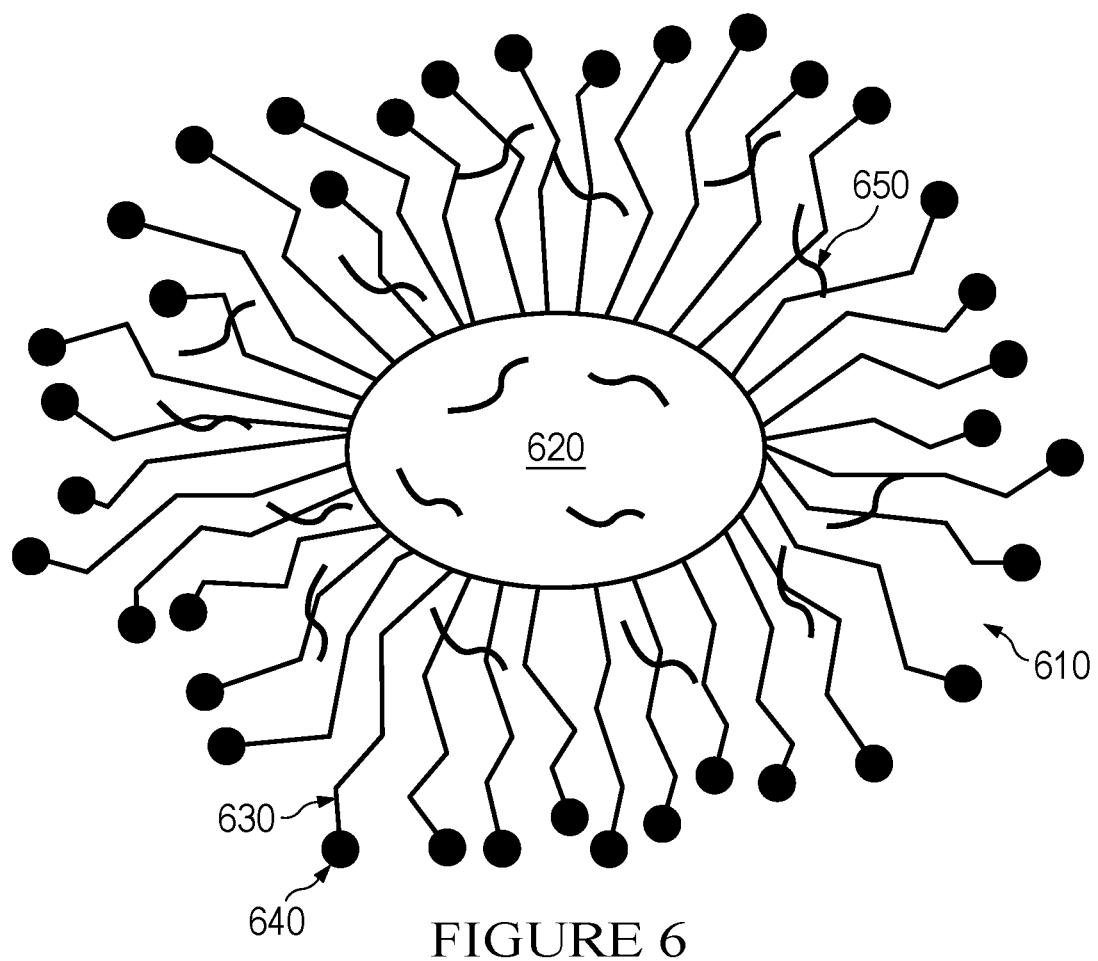

Turning now to FIG. 6, illustrated is a view of an embodiment of an activated cannabinoid controlled release compound. Analogous to FIG. 4 introduced above, the activated cannabinoid controlled release compound includes an exterior hosting layer 610, an internal layer 620 (e.g., an internal cannabinoid hosting layer), an amphoteric component tail 630, and an amphoteric component head 640. A surfactant 650 is added to form the activated cannabinoid controlled release compound (e.g., a mesoporous activated cannabinoid controlled release compound) and to facilitate an in situ extraction process of the absorbed cannabinoid.

Figure 7:
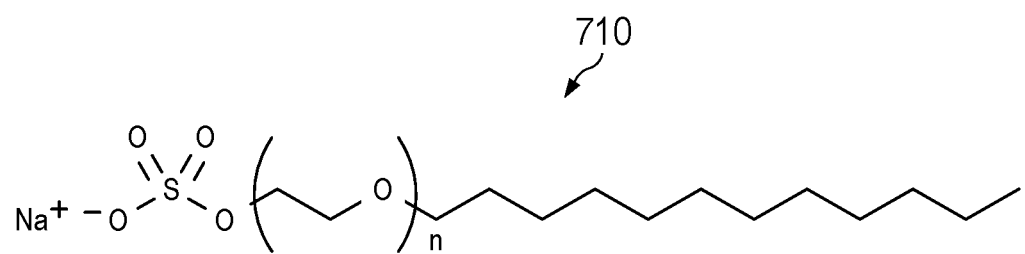
FIG. 7 illustrates a graphical chemical representation of an embodiment of one class of surfactant to form an activated cannabinoid controlled release compound.

Turning now to FIG. 7, illustrated is a graphical chemical representation of an embodiment of one class of surfactant ("surface active agent," 710) to form an activated cannabinoid controlled release compound. The surfactant 710 is an anionic surfactant, represented, without limitation, as sodium lauryl sulfate ("SLS"). The surfactant 710 is used in active cannabinoid controlled release compound to facilitate bioavailability of a cannabinoid by desorption from the compound.

Figure 8:
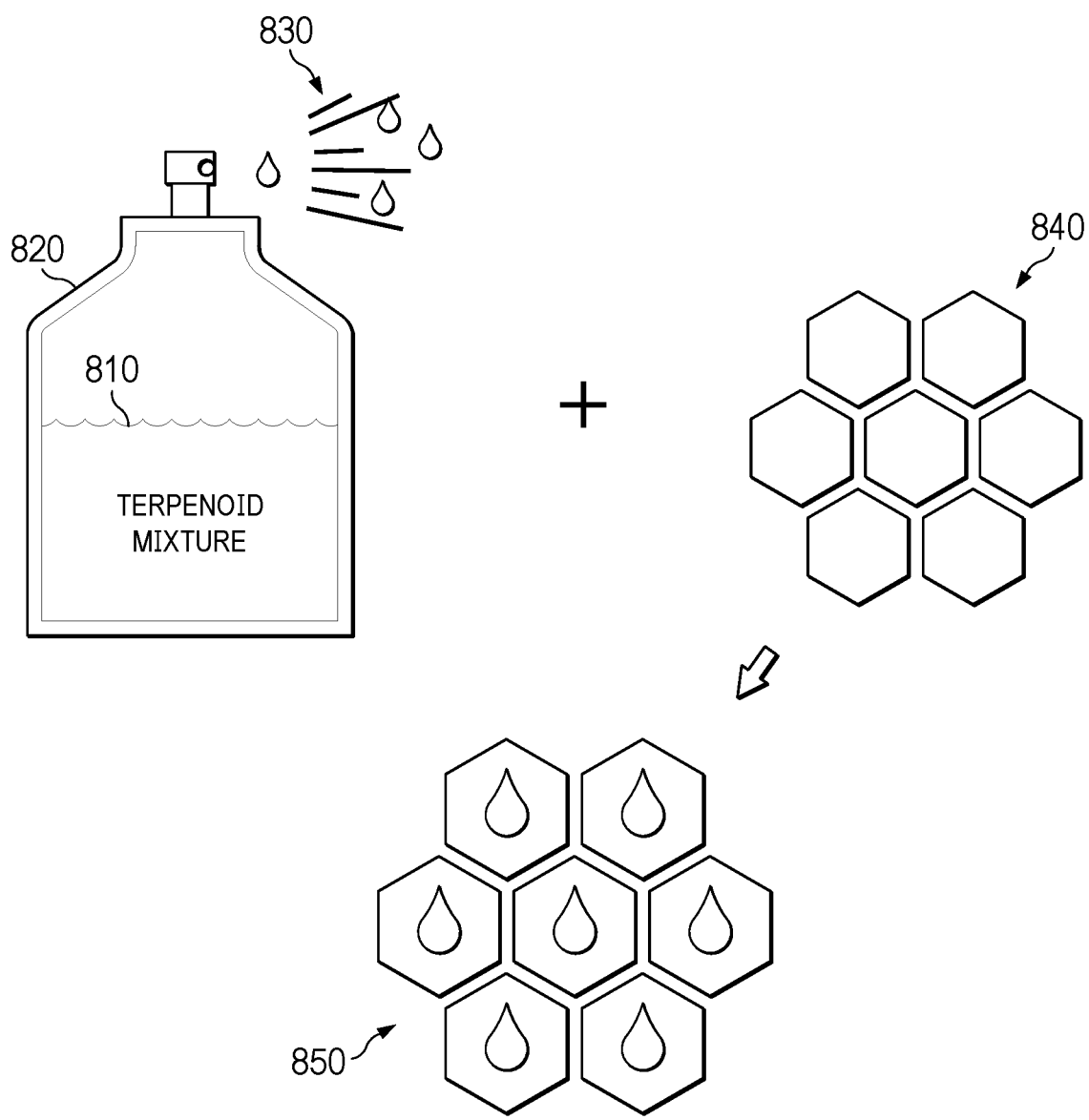
FIG. 8 illustrates a view of an embodiment of a sequence of steps demonstrating a terpenoid being infused into an activated cannabinoid controlled release compound.

Turning now to FIG. 8, illustrated is a view of an embodiment of a sequence of steps demonstrating a terpenoid (that can be a terpenoid mixture) 810 in a container 820 being infused into an activated cannabinoid controlled compound 840. The terpenoid 810 can be dispensed from the container 820 as, without limitation, a terpenoid spray 830. A prepared solution of terpenoid 810 is applied through either the spraying, a misting, atomizing, nebulizing, or liquid droplet operation to the formulated activated cannabinoid controlled release compound 840 to create a terpenoid infused, activated cannabinoid controlled release compound (a dry powder 850).

Figure 9:
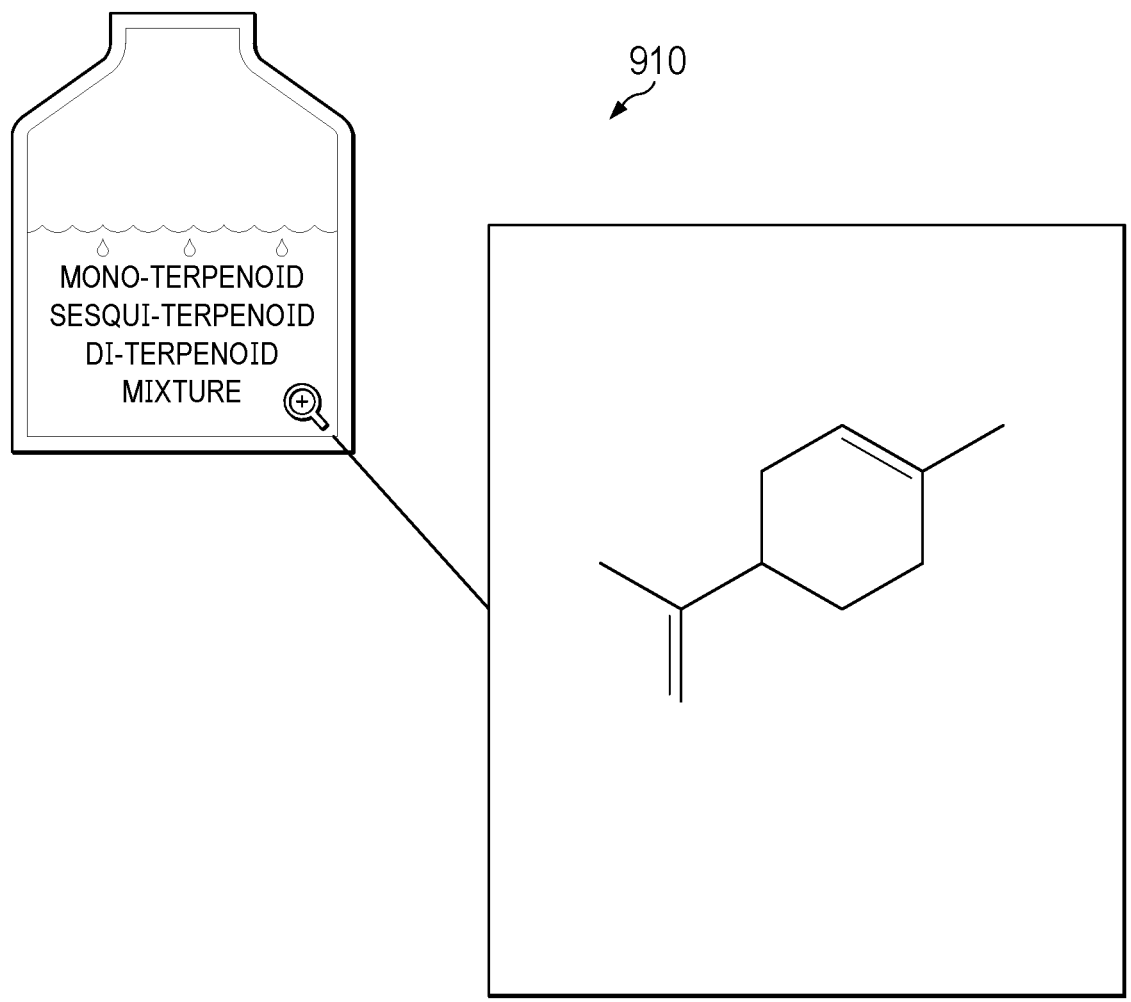
FIG. 9 illustrates a view of an embodiment demonstrating a terpenoid employed during a process of forming an activated cannabinoid controlled release compound.

Turning now to FIG. 9, illustrated is a view of an embodiment demonstrating a terpenoid (that can be a mixture) 910 employed during a process of forming an activated cannabinoid controlled release compound. The terpenoid 910 can include a mixture of individual terpenes/terpenoids. In an example, the terpenoid 910 is a complex mixture of terpenoids and/or other secondary small molecules. D-limonene $C_{10}H_{16}$ is an example of a monoterpene 910. Terpenoid classes defined in the mixture can contain, without limitation, monoterpenoid, sesquiterpenoid, diterpenoid, and triterpenoid molecules. Other small molecules can also be present in the defined terpenoid 910. Aldehydes, ketones, and esters are the major constituents of the other small molecules that can be present in the terpenoid 910. All of these components work in concert to provide organoleptic character to the finished formulated activated cannabinoid controlled release compound tablet.

Figure 10:
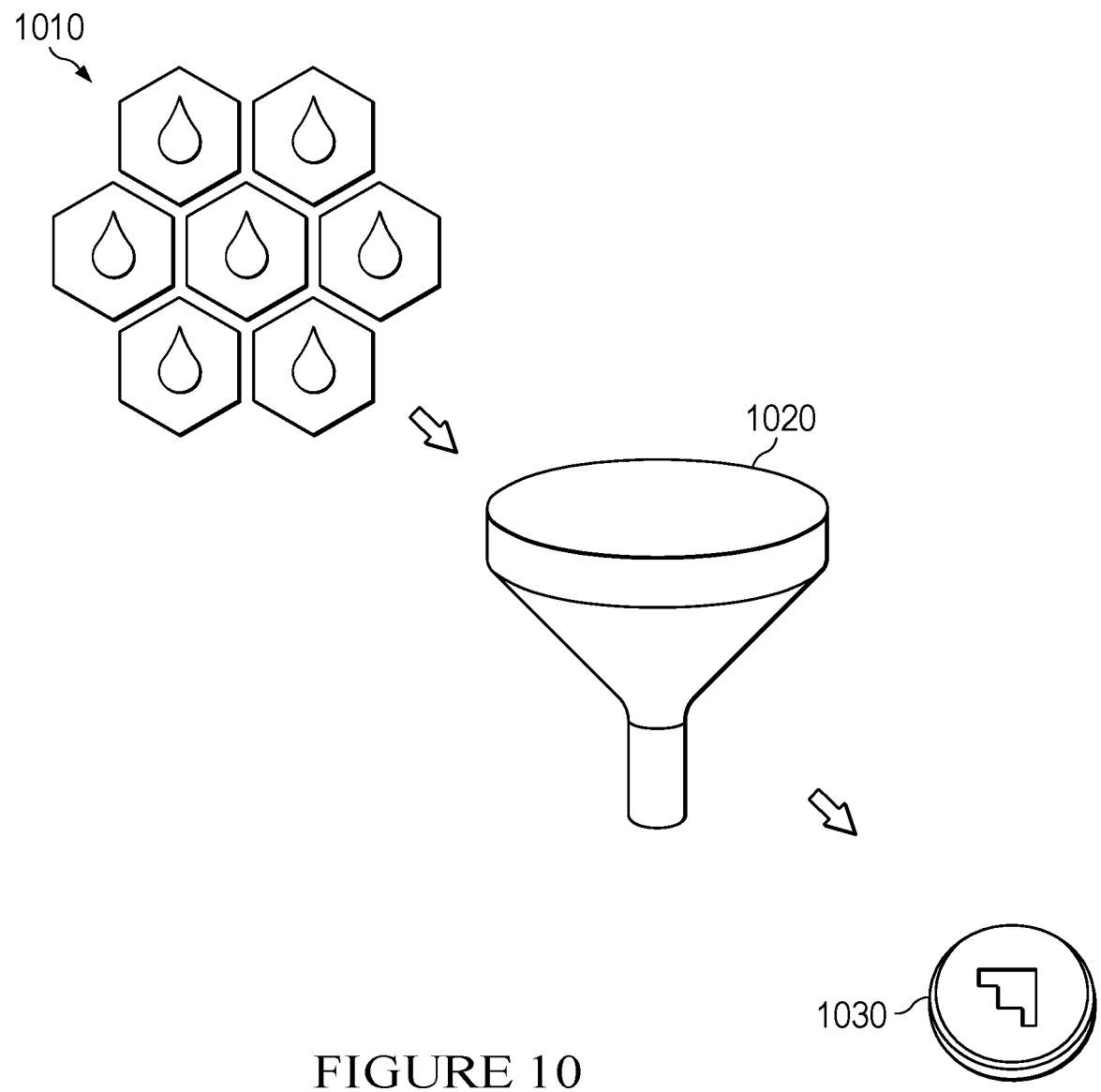
FIG. 10 illustrates a view of an embodiment demonstrating the formation of an activated cannabinoid controlled release compound tablet.

Turning now to FIG. 10, illustrated is a view of an embodiment demonstrating the formation of an activated cannabinoid controlled release compound tablet 1030. The activated cannabinoid controlled release compound tablet 1030 is formed by compression or compaction of the activated and terpenoid infused cannabinoid controlled release compound 1010. The activated and terpenoid infused cannabinoid controlled release compound 1010 is fed into a tableting instrument 1020 to compress the activated and terpenoid infused cannabinoid controlled release compound 1010 into the activated cannabinoid controlled release compound tablet 1030.

Figure 11:
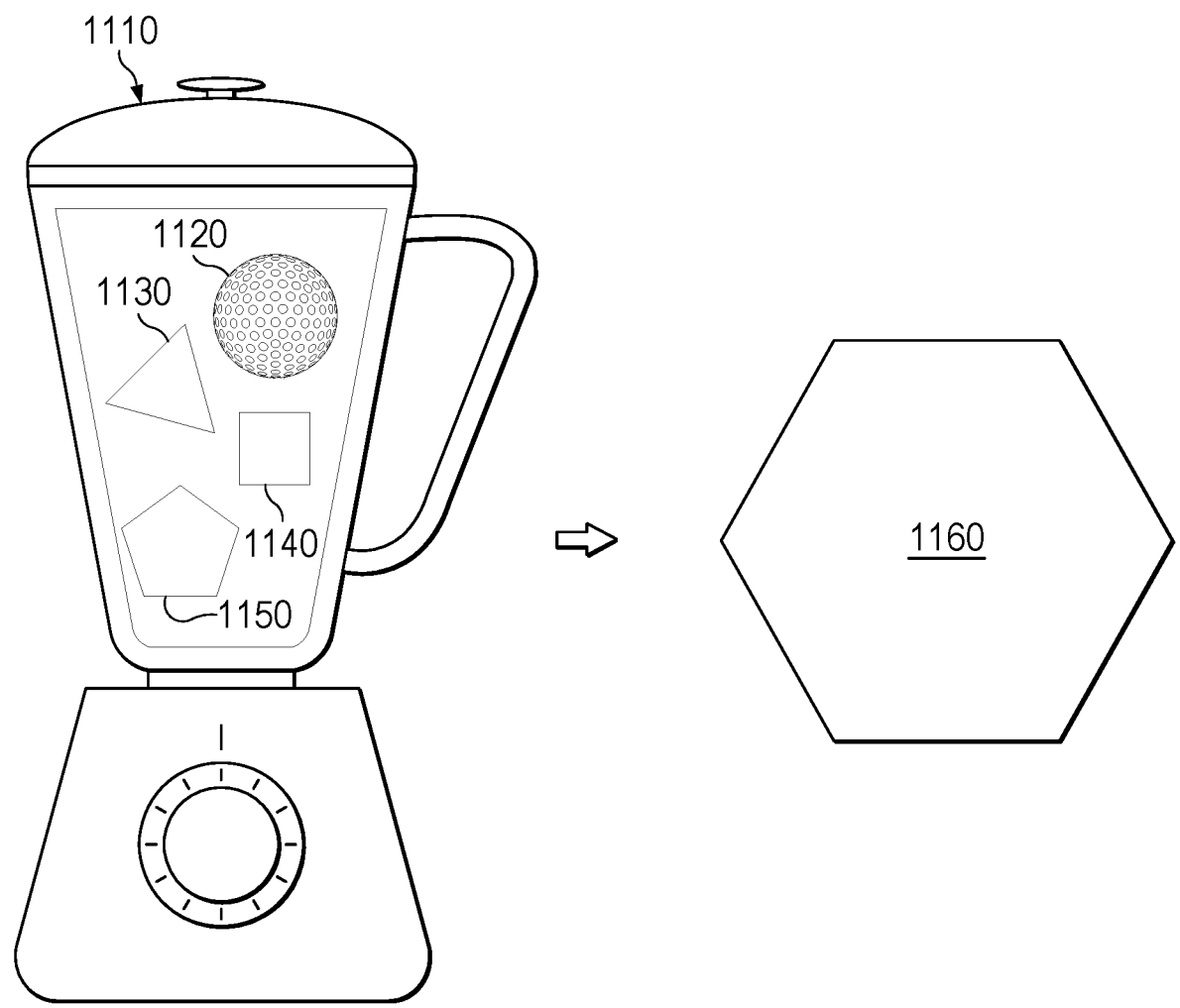
FIG. 11 illustrates a view of an embodiment demonstrating a process for formulation of an activated cannabinoid controlled release compound.

Turning now to FIG. 11, illustrated is a view of an embodiment demonstrating a process for formulation of an activated cannabinoid controlled release compound 1160. The formulation is achieved by blending and mixing the individual excipients together in a high shear blender 1110. Order of addition can play a role in final potency and optimized behavior of the activated cannabinoid controlled release compound 1160, but this illustrative example simply shows a process where a terpenoid infused activated cannabinoid controlled release compound 1120 is mixed with sodium croscarmellose 1130 followed by microcrystalline cellulose 1140 followed by a powder lubricant 1150. This process for powder formulation is followed by compression or compaction of the activated cannabinoid controlled release compound 1160 to produce the tablet (such as the activated cannabinoid controlled release compound tablet 1030 introduced with respect to FIG. 10).

The following is a description of processes for converting a cannabinoid active pharmaceutical ingredient ("cAPI") into a free-flowing powder (an activated cannabinoid controlled release compound) suitable for tableting. A cannabis API distillate can be used to produce, without limitation, the following cannabinoid forms:
 i. delta-9 tetrahydrocannabinol;
 ii. delta-8 tetrahydrocannabinol;
 iii. delta-11 tetrahydrocannabinol;
 iv. delta-9 tetrahydrocannabivarin;
 v. delta-8 tetrahydrocannabivarin;
 vi. delta-11 tetrahydrocannabivarin
 vii. cannabinol;
 viii. 11-hydroxy-cannabinol;
 ix. 11-hydroxy-cannabivarin;
 x. cannabichromene;
 xi. cannabigerol;
 xii. cannabidiol;
 xiii. 11-hydroxy-delta-9-tetrahydrocannabinol;
 xiv. 11-hydroxy-delta-9-tetrahydrocannabivarin;
 xv. 11-hydroxy-delta-8-tetrahydrocannabinol; and
 xvi. 11-hydroxy-delta-8-tetrahydrocannabivarin.

The cAPI can be isolated in the form of a polymorphous crystalline solid, an amorphous granular solid, or a powdery, colorless solid, listed below, that is employed to produce a tablet:
 i. delta-9-tetrahydrocannabinolic acid;
 ii. delta-8 tetrahydrocannabinolic acid;
 iii. delta-9-tetrahydrocannabivarinic acid;
 iv. delta-8 tetrahydrocannabivarinic acid;
 v. cannabidiol;
 vi. cannabidiolic acid;
 vii. cannabigerol;
 viii. cannabigerolic acid; and
 ix. cannabinchromenic acid.

Figure 12:
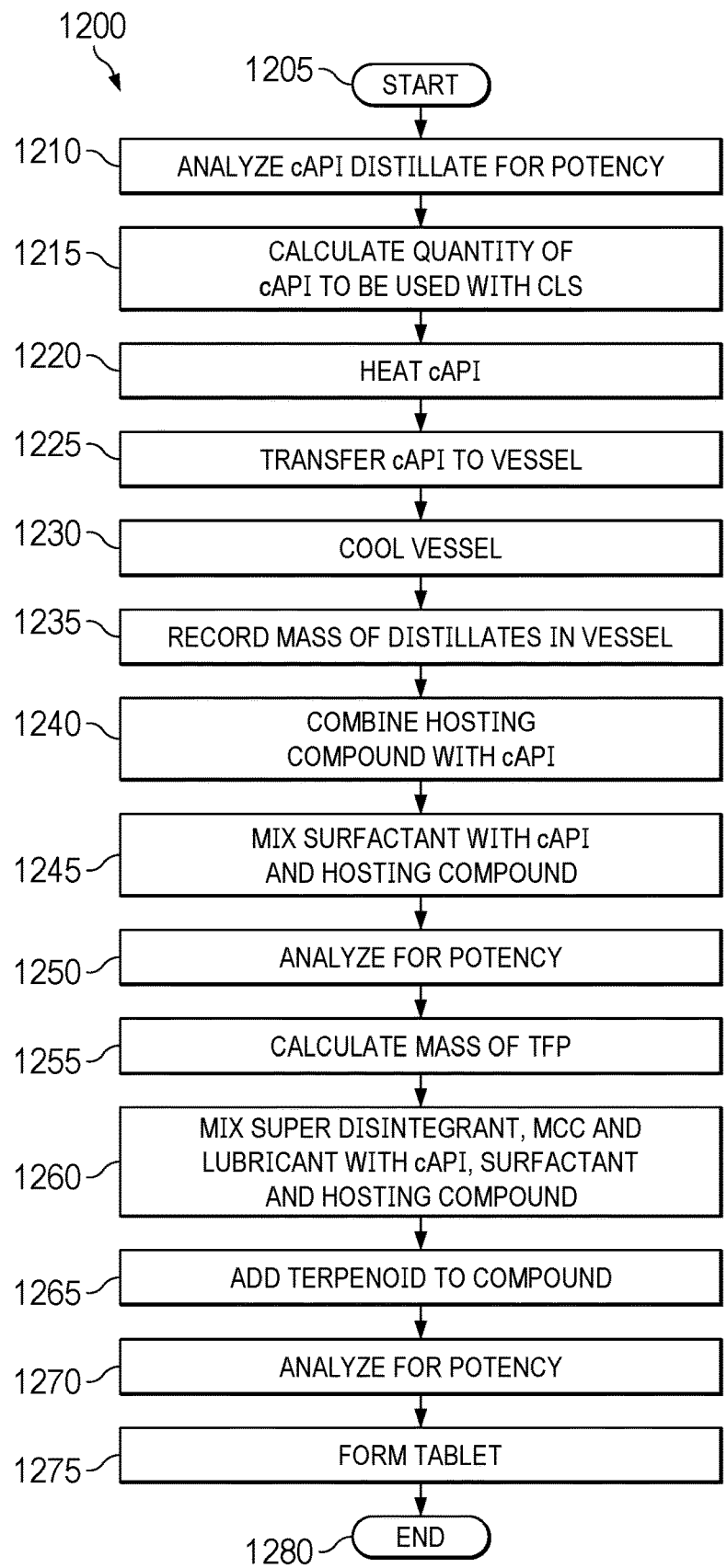
FIG. 12 illustrates a flow diagram of an embodiment of a method of forming an activated cannabinoid controlled release compound tablet.

Turning now to FIG. 12, illustrated is a flow diagram of an embodiment of a method 1200 of forming an activated cannabinoid controlled release compound tablet including a cannabinoid active pharmaceutical ingredient ("cAPI"). The method begins at a step 1205. At a step 1210, the method 1200 includes analyzing a cAPI (e.g., the cAPI distillate) for potency through, for instance, high performance liquid chromatography ("HPLC"), gas chromatography ("GC") or mid-infrared chromatography. The analysis determines what percentage of cannabinoid is included in the analyte. A potency/purity objective, without limitation, is 65 to 95 percent ("%") purity.

When amorphous cannabinoid containing ballast (naturally occurring lipids, waxes, cellular wall components) is used as cAPI, the potency/purity objective, without limitation, is 65 to 85 percent ("%") purity. Ballast cAPI does not need added surfactant to properly load or desorb from the silica. The naturally occurring compounds retained in the cAPI exhibit the same properties as observed with an added surfactant. This may be occurring through the surfactant like qualities of the phospholipid bilayer found within the remnants of the plant cell wall. In order to extract said cannabinoid from the cannabis plant, the cell wall is lysed, resulting in carry-over of lysed cell wall components.

At a step 1215, the method 1200 includes calculating the quantity of cAPI to be used with a cannabinoid loaded silica ("CLS"). At a step 1220, the method 1200 includes heating the cAPI to, without limitation, about 95 to 100 degrees Celsius ("C") for approximately 45 to 60 minutes. At a step 1225, the method 1200 includes transferring the cAPI to a nonreactive/non-stick vessel of known capacity such as a food-grade silica/silicane vessel.

At a step 1230, the method 1200 includes cooling the charged cAPI vessel to, for instance, lower than about −10 degrees C. for about 10 to 16 minutes to cool the cAPI. At a step 1235, the method 1200 includes recording a mass of each distillate in the charged cAPI vessel. In particular, masses of the empty vessel and the charged vessel are recorded to indicate the quantity of distillate in the charged vessel. At a step 1240, the method 1200 includes combining (or mixing) a hosting compound such as mesoporous silica with the cAPI (the cannabinoid) in, for instance, a blender or granulator. Other possible hosting compounds include, without limitation, amorphous silica nanoparticles ("ASN"), ceramic nanoparticles ("CNP"), polymeric micelles, drug encapsulated polymeric nanoparticles, lipid polymer hybrid nanoparticles, lipid based nanoparticles, solid lipid nanoparticles ("SLN"), and mesoporous alumina. The components in the blender or granulator are blended, without limitation, at about 1,000 to 30,000 revolutions-per-minute ("rpm") for 1 to 30 minutes. The cannabinoid is thereby loaded onto the mesoporous silica (or other hosting compound) and inside pores of the mesoporous silica. Molecular interactions keep the cannabinoid and the mesoporous silica tightly bound together. The combination of the cAPI with a hosting compound forms a cannabinoid controlled release compound.

In accordance with adding the hosting compound, the cannabinoid controlled release compound may be filtered through, for instance, 600 micron ("μm") sieve to remove the larger particles. The powdery compound is then combined and homogenized.

At a step 1245, the method 1200 includes mixing a surfactant (surface active agent) to the mixture of the cAPI and mesoporous silica (the cannabinoid controlled release compound) within a blender or granulator at, for instance, 100-30000 rpm for 5-30 minutes. The surfactant molecule generally has a hydrophilic (water attracting) end and a hydrophobic (water repelling/fat attracting) end, which is a common detergent structure. The mesoporous silica exhibits some fatty characteristics. This structure helps the user's body to extract the cannabinoid from the mesoporous silica (or other hosting compound). The result is improved bioavailability of the cannabinoid in the user. The surfactant may include anionic surfactants, cationic surfactants, and polymeric surfactants. The anionic surfactants include, without limitation, sodium lauryl sulfate ("SLS"), sodium lauryl ethyl sulfate ("SLES"), and ammonium lauryl sulfate ("ALS"). The cationic surfactant may include methyl triethanolammonium ("MTEA"). The polymeric surfactants include, without limitation, polyEO-PolyPO block copolymers, and alkyl glycosides.

The combination of the surfactant with the cannabinoid controlled release compound forms an activated cannabinoid controlled release compound (also referred to as a total formulated powder ("TFP")). In accordance with adding the surfactant, the activated cannabinoid controlled release compound may be filtered through, for instance, 600 micron ("μm") sieve to remove the larger particles. The powdery compound is then combined and homogenized.

At a step 1250, the method 1200 includes analyzing the activated cannabinoid controlled release compound for potency. The homogenous batch is randomly sampled and potency tested in triplicate. A target potency is greater than 28% cAPI, within 5% relative standard deviation ("RSD"). A desired target loading of the cAPI on mesoporous silica, by mass, is about 35% to 70%. These loadings enable a reasonably small cannabinoid tablet to be produced with a desired pharmacological effect. A tablet with such loading can have 25 milligrams ("mg") of a drug API loaded into a tablet of 175 mg total mass, which is 14% API loading by mass.

At a step 1255, the method 1200 includes calculating excipient masses exclusive of the cannabinoid masses for the activated cannabinoid controlled release compound (a total formulated powder ("TFP")). At a step 1260, the method 1200 includes mixing sodium croscarmellose (a super disintegrant such as the commercial product "Ac-Di-Sol"), microcrystalline cellulose ("MCC", a vegan excipient to take up volume when the tablet is compressed), and a lubricant with the activated cannabinoid controlled release compound. The super disintegrant enables the tablet to break apart quickly in the digestive system of a user, and generally increases bioavailability of the constituents. The lubricant may include, without limitation, magnesium stearate and hydroxymethyl cellulose or other long-chain fatty acid in a small percentage to the compound to prevent the tablet powder from being too sticky to the tableting device when the tablet is formed by compression. The lubricant also has a beneficial effect on the free-flowing properties of the cannabinoid-bearing powder. Another lubricant that can be used is hydroxymethyl cellulose. Again, the activated cannabinoid controlled release compound is mixed with the MCC, the super disintegrant, and the lubricant, and the batch is mixed to form a TFP. In accordance with the aforementioned step, the TFP is homogenized, and a small aliquot is removed and the lubricant, which is sieved into the whole batch and homogenized. Once all particles are less than 600 μm, the powder is combined and homogenized.

At a step 1265, the method 1200 includes adding and homogenizing a steam-distilled terpenoid from a Cannabis Sativa plant to and with the activated cannabinoid controlled release compound to form a dry powder. The terpenoid is an oil present in a cannabis plant with organoleptic and pharmacological properties that can enhance a user's targeted effect in response to a cannabinoid. In accordance with the aforementioned step, the activated cannabinoid controlled release compound may be homogenized, and a small aliquot is removed and the lubricant, which is sieved into the whole batch and homogenized. Once all particles are less than 600 μm, the powder is combined and homogenized. The terpenoid includes, without limitation, monoterpenoid (e.g., alpha-pinene and linalool), sesquiterpenoid (e.g., farnesene and nerolidol), diterpenoid (e.g., cembrene A and phytol), and triterpenoid (e.g., squalene).

At a step 1270, the method 1200 includes analyzing the resulting mixture for potency. A target potency is, without limitation, 14.3%, based on 175 mg total tablet mass and 25 mg cAPI mass with +/−10% cAPI within 5% RSD. At a step 1275, the method 1200 includes forming a tablet by dry compression of the powder with a tool to produce a relatively stable product without loss of potency over time and with a desired pharmacological effect on a user. In other words, the dry powder of the activated cannabinoid controlled release compound is compressed to form the activated cannabinoid controlled release compound tablet. The method 1200 concludes at an end step 1280.

The following examples provide different compositions of embodiments of the activated cannabinoid controlled release compound tablet. In accordance with selected representative examples, FIGS. 13 to 28 illustrate graphical representations of embodiments of potencies of the cannabinoid (in milli-absorbance unit ("mAU") versus minutes ("min.") at steps 1210, 1250 and 1270 of the method 1200 of forming an activated cannabinoid controlled release compound tablet described with respect to FIG. 12. It should also be understood that selected steps may be omitted (such as the step 1245) from the method 1200 to form the activated cannabinoid controlled release compound tablet.

A high performance liquid chromatography ("HPLC") method is used to analyze feedstock material, cannabinoid-loaded silica, and formulated powder for 25-mg active cannabinoid-loaded tablet for the following analyses. A solvent system using a Shimadzu LC-20AT/SIL20A HT/CBM-10A/SPD-20A composed of a ratio of 1:3 water:acetonitrile, with 0.1 volume by volume ("v/v") percent formic acid. A Phenomenex Luna Omega 3 μm Polar C18 100 LC, 1504.6 millimeter ("mm") column is used. The flow rate for the solvent pumps are 1.200 milliliters per minute ("mL/min"). The absorbance of the ultraviolet violet/visible light spectrum ("UV/VIS") is 230 nm and retention time for each run is 15.01 min.

Regarding the extraction of the cannabinoid for the preparation of the HPLC analysis, a 100 mg of cannabinoid of interest is diluted to the fill line of a 10.0 mL volumetric flask in methanol and mixed via vortex. This extract is diluted 1:9 in methanol in a 1.5 mL microcentrifuge tube. The tube is vortexed for 10 seconds and then diluted 1:9 in a 1.5 mL HPLC vial. The HPLC vial is vortexed for 10 seconds before final analysis.

Regarding the extraction of the cannabinoid-loaded silica for preparation of the HPLC analysis, a 200 mg of cannabinoid-loaded silica of interest is diluted to the fill line of a 10.0 mL volumetric flask in methanol and mixed via vortex. After 1-12 hours, this extract is filtered via 0.45 μm polytetrafluoroethylene ("PTFE") syringe filters into a 1.5 mL microcentrifuge tube. The filtered solution is then diluted 1:9 in methanol in a 1.5 mL microcentrifuge tube. The tube is vortexed for 10 seconds and then diluted 1:9 in a 1.5 mL HPLC vial. The HPLC vial is vortexed for 10 seconds before final analysis.

Regarding of the extraction of the formulated powder to be compressed into tablets for the preparation of the HPLC analysis, a 400 mg of formulated powder of interest to be compressed into tablets is diluted to the fill line of a 10.0 mL volumetric flask in methanol and mixed via vortex. After 1-12 hours, this extract is filtered via 0.45 μm PTFE syringe filters into a 1.5 mL microcentrifuge tube. The filtered solution is then diluted 1:9 in methanol in a 1.5 mL microcentrifuge tube. The tube is vortexed for 10 seconds and then diluted 1:9 in a 1.5 mL HPLC vial. The HPLC vial is vortexed for 10 seconds before final analysis.

EXAMPLE 1

A cannabinoid-loaded silica ("CLS") is prepared via high-shear blending. The composition of the CLS is described in Table 1.

TABLE 1

| Composition of CLS | |
|---|---|
| Component | wt. % |
| Cannabinoid[1] | 30-75 |
| Silicon dioxide | 25-70 |
| Surfactant | 0-4 |

[1]cannabinoid potency will determine total cannabinoid loading

A granulation containing cannabinoid, silicon dioxide (silica) and surfactant is combined at 40% cannabinoid loading concentration. The amount of cannabinoid was measured based of potency analysis by HPLC (see FIGS. 13 to 17, 26), combined with pre-measured mass of silica, and mixed until completely homogenous. Homogeneity was achieved in 60 to 270 seconds (depending on cannabinoid). The appropriate amount of surfactant is added to the granulation and blended for an additional 60 seconds. When homogeneity was achieved, all materials are removed and transferred to a 20 μm to 600 μm vibratory sieve. When possible, an ultrasonic and vibratory sieve is used to increase efficacy of sieving. The cannabinoid loaded silica ("CLS") potencies are analyzed using HPLC (see FIGS. 18 to 22, 27).

EXAMPLE 2

A cannabinoid-containing silica (CLS-1) is prepared via high-shear blending. The composition of CLS using an amorphous resinous cannabinoid is described in Table 2.

TABLE 2

Composition of CLS-1

| Component | wt. % |
|---|---|
| Cannabinoid | 39.6 |
| Silicon dioxide | 59.9 |
| Surfactant | 0.5 |

Figure 18:
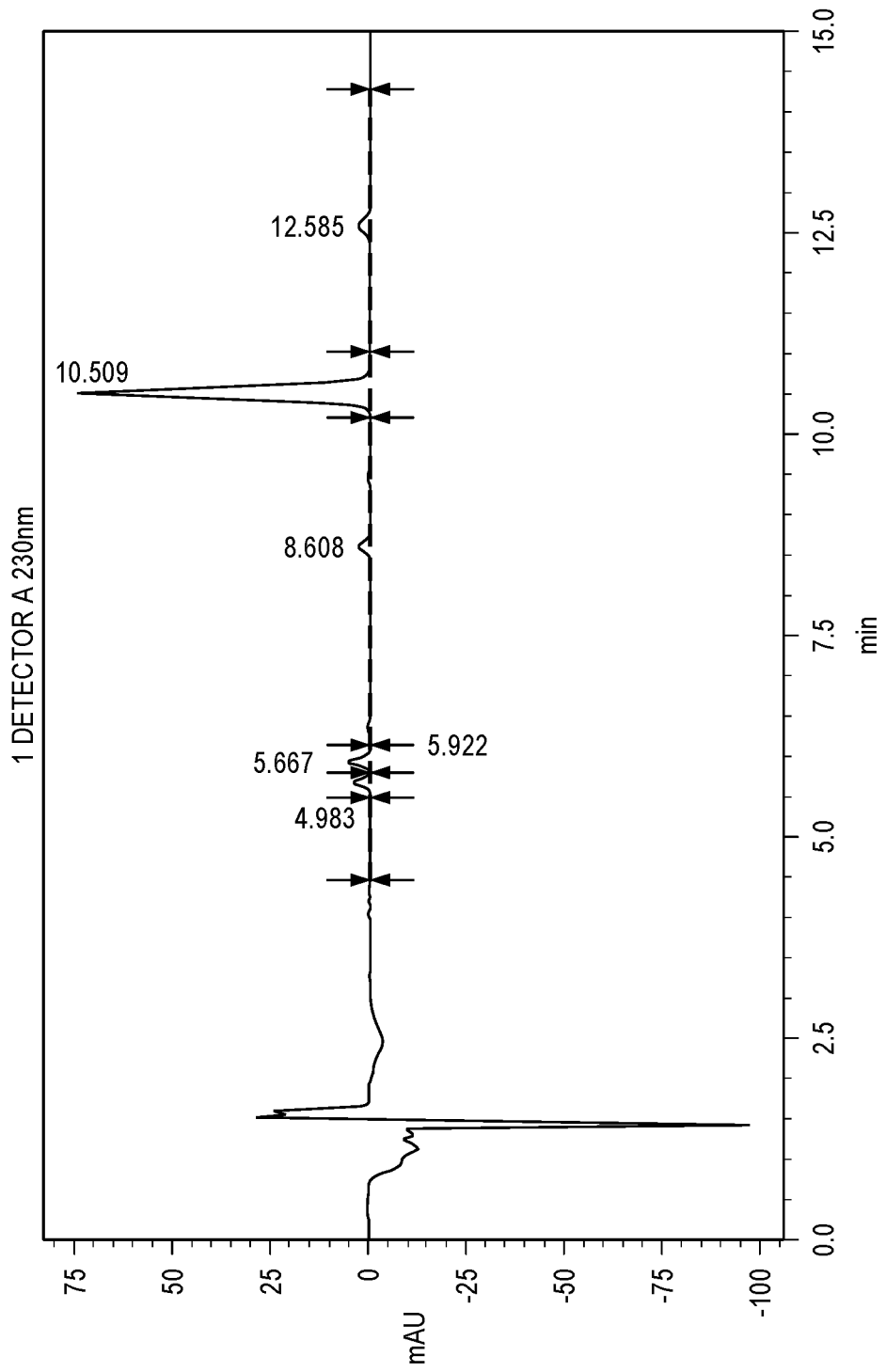

A granulation containing amorphous resinous cannabinoid, silicon dioxide and surfactant is combined at 35.6 percent cannabinoid loading concentration. Amorphous resinous cannabinoid (e.g., Δ9-tetrahydrocannabinol, FIG. 13) is heated in the oven [at 80 to 120° C.] until desired viscosity is achieved. Resinous cannabinoid is transferred to appropriate vessel and covered to prevent addition of adventitious water. The vessels are cooled [at −40 to −80° C.] for 0 to 1 hours. The amount of cannabinoid is measured, combined with pre-measured mass of silica, and mixed until completely homogenous. Homogeneity is achieved in 90 seconds to 270 seconds (depending on cannabinoid). When the granulation is completely homogenous, surfactant is added to the granulation and blended for an additional 60 seconds. When homogeneity is achieved, all materials are removed and transferred to a 600 μm ultrasonic and vibratory sieve. The cannabinoid loaded silica-1 (CLS-1) potency is analyzed using HPLC (FIG. 18).

EXAMPLE 3

A cannabinoid-loaded silica (CLS-2) is prepared via high-shear blending. The composition of CLS using a polymorphous or crystalline cannabinoid is described in Table 3.

TABLE 3

Composition of CLS-2

| Component | wt. % |
|---|---|
| Cannabinoid | 70.0 |
| Silicon dioxide | 29.5 |
| Surfactant | 0.5 |

Figure 19:
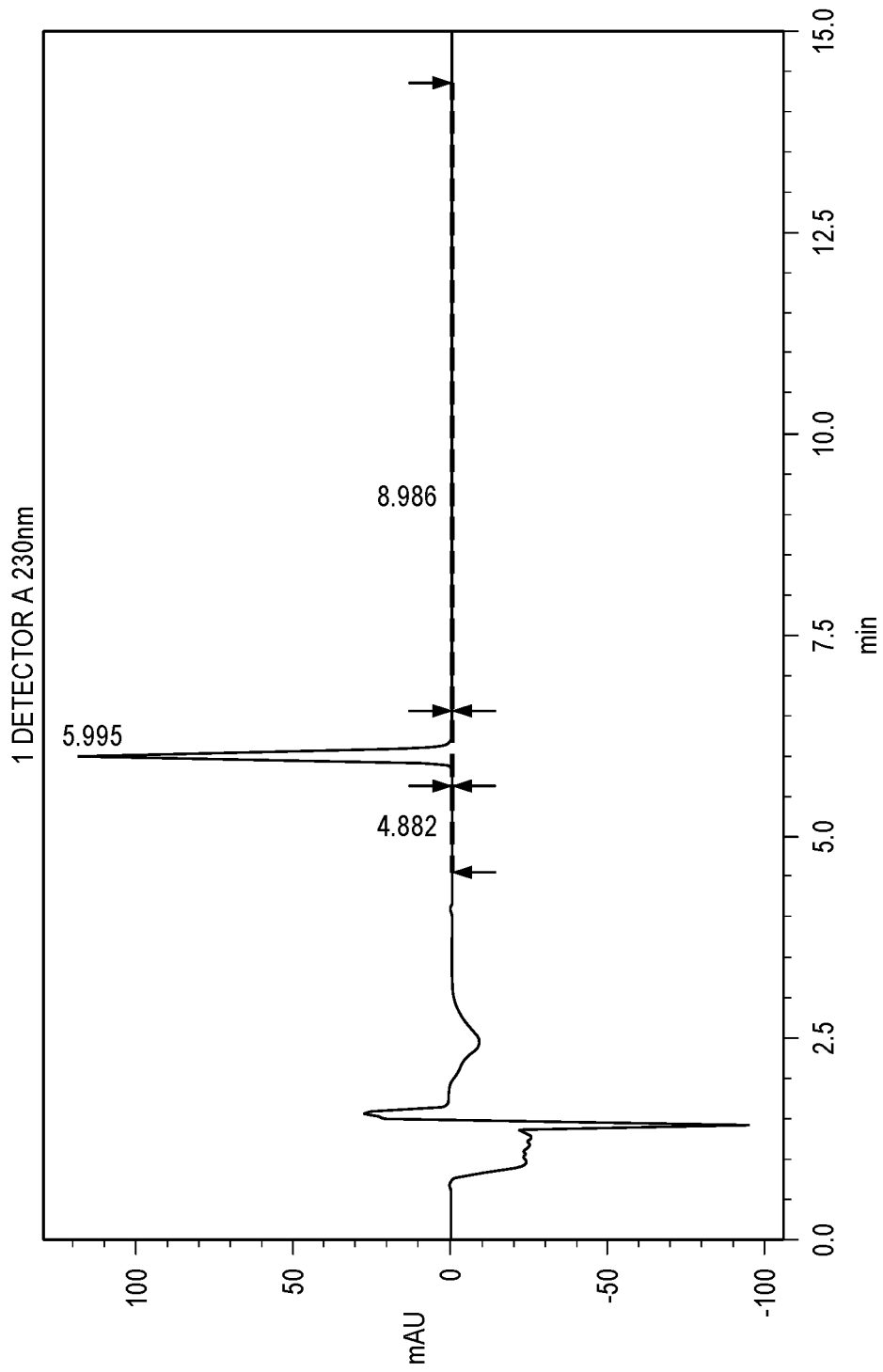

A granulation containing polymorphous or crystalline cannabinoid (FIG. 14), silicon dioxide and surfactant is combined at 70% cannabinoid loading concentration. The amount of cannabinoid is measured, combined with pre-measured mass of silica, and mixed until completely homogenous. Homogeneity is achieved in 60 to 180 seconds (depending on cannabinoid). The appropriate amount of surfactant is added to the granulation and blended for an additional 60 seconds. When homogeneity is achieved, all materials are removed and transferred to a 600 μm ultrasonic and vibratory sieve. The cannabinoid loaded silica—2 (CLS-2) potency is analyzed using HPLC (FIG. 19).

EXAMPLE 4

An amorphous resinous cannabinoid-loaded silica obtained in Example 2 is blended with excipients and directly compressed into tablets including 25 mg of active cannabinoid for oral administration. The composition of the powder and compressed tablet is described in Table 4.

TABLE 4

Composition of formulated powder

| Component | wt. % |
|---|---|
| CLS-1 | 38.5 |
| Microcrystalline Cellulose | 55.2 |
| Croscarmellose Sodium | 5.0 |
| Magnesium Stearate | 1.0 |
| Terpenoid | 0.3 |

Figure 23:
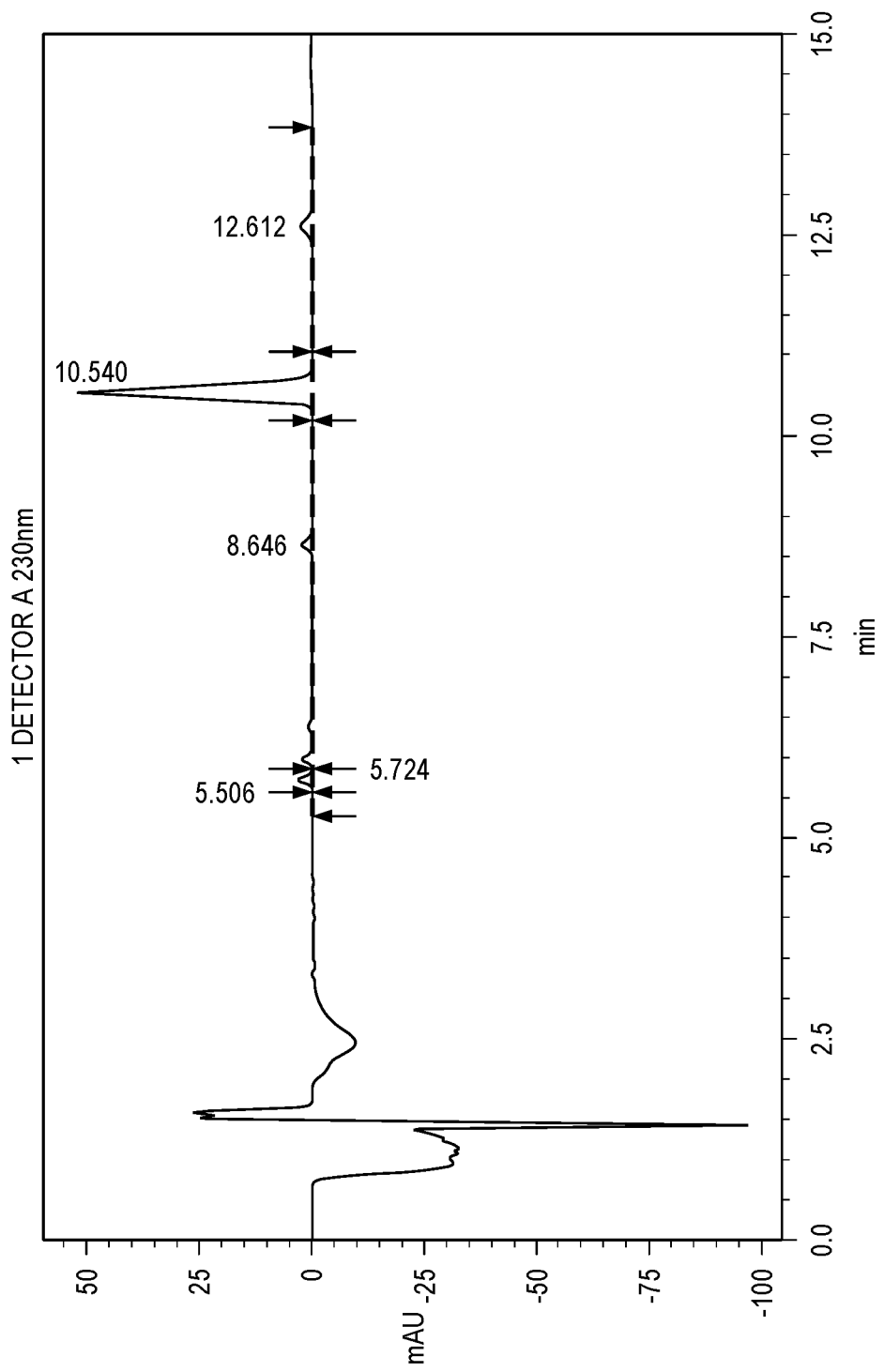

The compressed tablets have an average weight of 175 mg and composed of 38.1 wt. % of CLS-1, 55.2 wt. % of microcrystalline cellulose, 5.0 wt. % of croscarmellose sodium, 1.0 wt. % of lubricant, and 0.3 wt. % terpenoid mixture. The tablets are quality-controlled for specifications (described in Table 7 below) and stored in appropriate containers. The total formulated powder ("TFP") cannabinoid potency is analyzed using HPLC (FIG. 23).

EXAMPLE 5

A polymorphous or crystalline cannabinoid-loaded silica obtained in Example 3 is blended with excipients and directly compressed into tablets comprising 25 mg of active cannabinoid (e.g., Δ9-tetrahydrocannabinolic acid) for oral administration. The composition of the powder and compressed tablet is described in Table 5.

TABLE 5

Composition of formulated powder

| Component | wt. % |
|---|---|
| CLS-2 | 21.5 |
| Microcrystalline Cellulose | 72.2 |
| Croscarmellose Sodium | 5.0 |
| Magnesium Stearate | 1.0 |
| Terpenoid | 0.3 |

Figure 24:
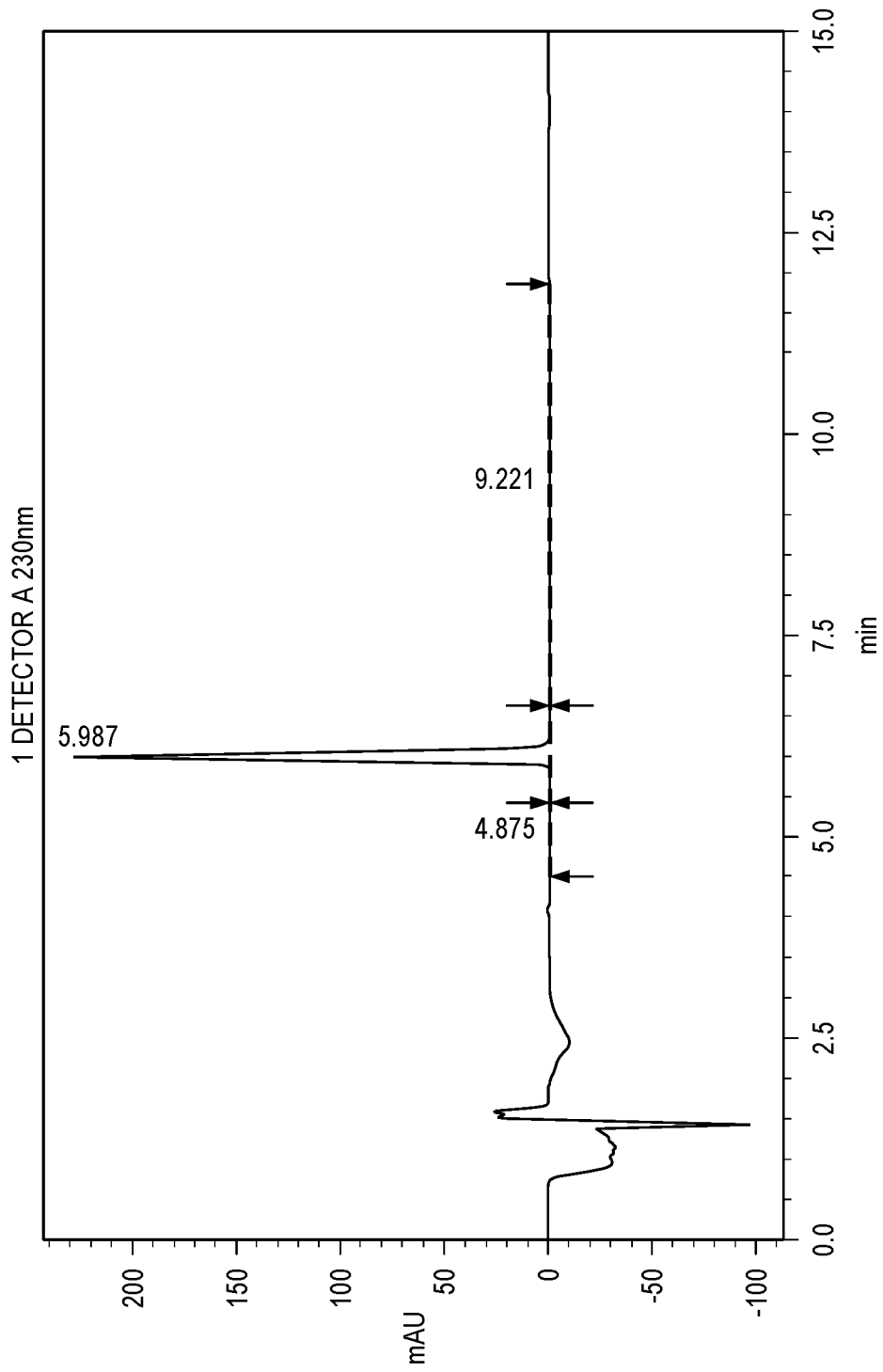

The compressed tablets have an average weight of 175 mg and composed of 21.5 wt. % of CLS-2, 72.2 wt. % of microcrystalline cellulose, 5.0 wt. % of croscarmellose sodium, 1.0 wt. % of lubricant, and 0.3 wt. % terpenoid mixture. The tablets are quality-controlled for specifications (described in Table 7 below) and stored in appropriate containers. The total formulated powder ("TFP") cannabinoid potency is analyzed using HPLC (FIG. 24).

EXAMPLE 6

Cannabinoid-loaded silica obtained in Example 2 and Example 3 are blended with excipients and directly compressed into tablets comprising 25 mg of total active cannabinoid for oral administration. The composition of the powder and compressed tablet is described in Table 6.

TABLE 6

Composition of formulated powder

| Component | wt. % |
|---|---|
| CLS-1 | 5.1 |
| CLS-2 | 9.7 |
| CLS-2 | 9.7 |
| CLS-2 | 15.5 |
| Microcrystalline Cellulose | 54.0 |
| Croscarmellose Sodium | 5.0 |
| Magnesium Stearate | 1.0 |

Figure 25:
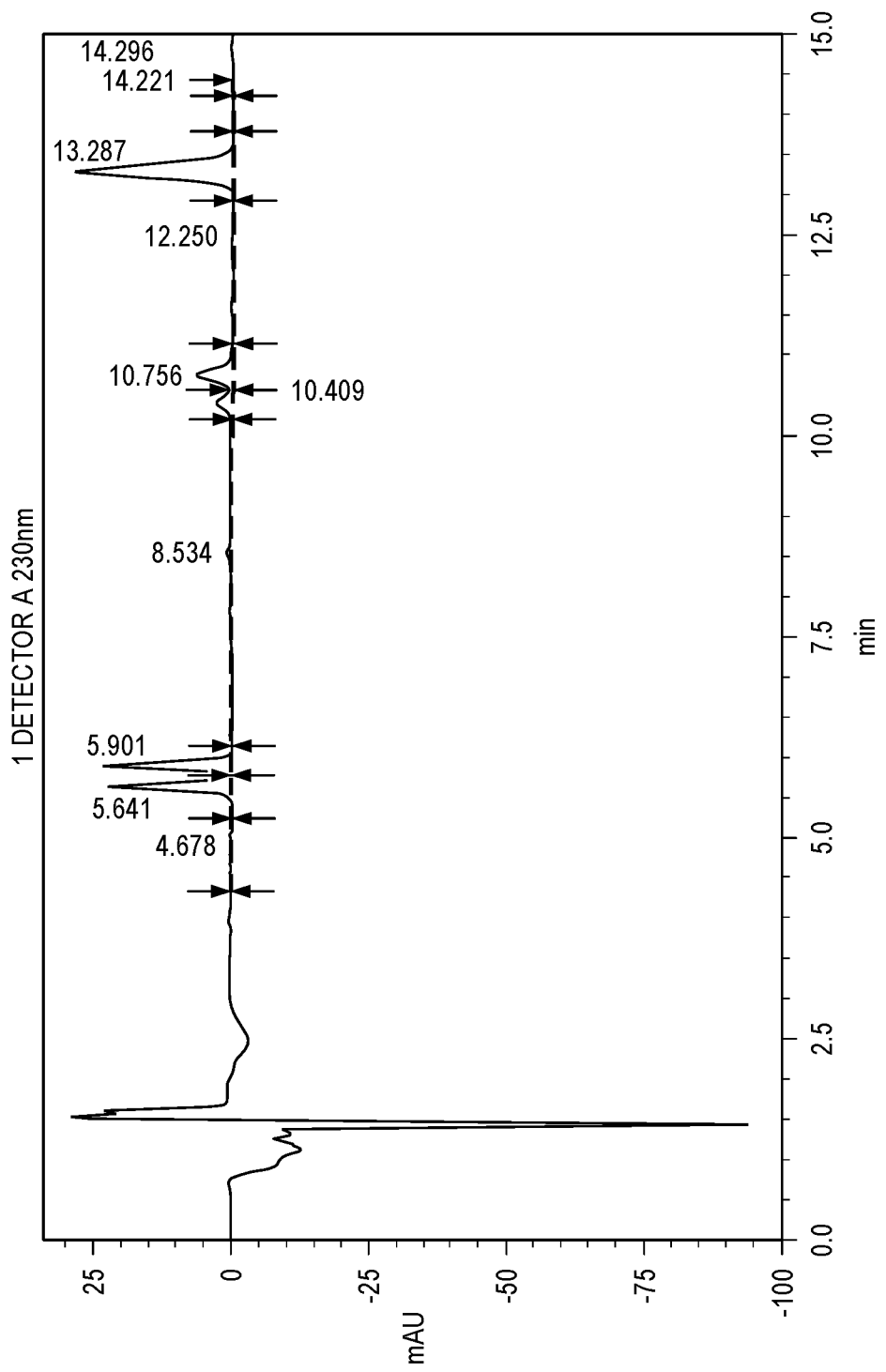

The compressed tablets have an average weight of 175 mg and composed of 5.1 wt. % of CLS-1, 9.7 wt. % of CLS-2, 9.7 wt. % of CLS-2, 15.5 wt. % of CLS-2, 54.0 wt. % of microcrystalline cellulose, 5.0 wt. % of croscarmellose sodium, and 1.0 wt. % of lubricant. The tablets are quality-controlled for specifications (described in Table 7 below) and stored in appropriate containers. The total formulated powder ("TFP") cannabinoid potency are analyzed using HPLC (FIG. 25).

TABLE 7

Specification of Tablets

| Parameter | Method | Specification |
|---|---|---|
| Hardness | USP <1217> | ≤65N ≥ 40N |
| Diameter | — | 8 mm |
| Cannabinoid Content | HPLC | 5%-25% |
| Dissolution | USP <711> | ≥80% (Q) within 20 min |
| Disintegration | USP <701> | <5 minutes |

Figure 13:
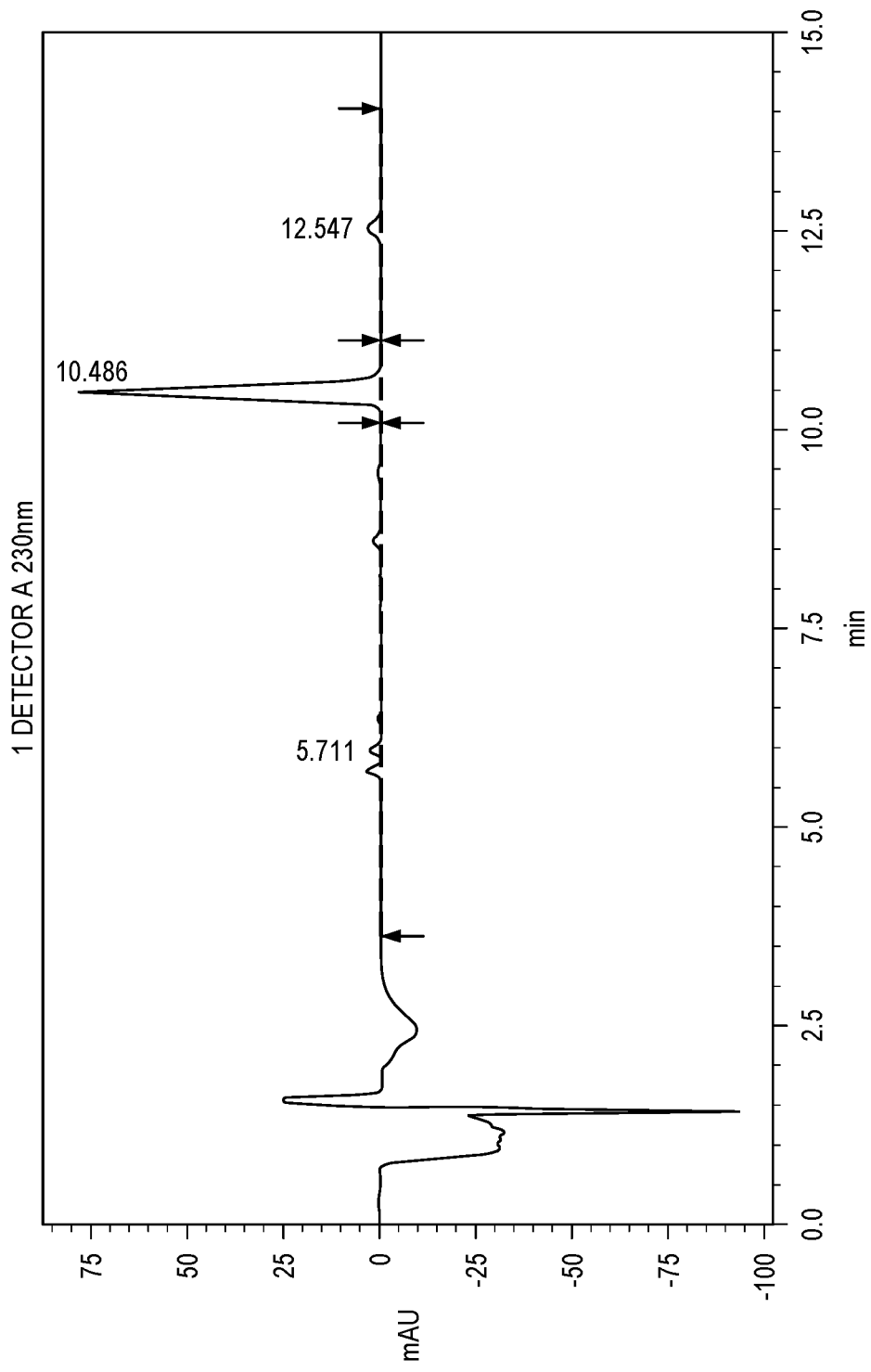
FIGS. 13 to 28 illustrate graphical representations of embodiments of potencies of a cannabinoid for representative examples.

With respect to FIGS. 13 to 25 and with continuing reference to FIG. 12, the chromatogram shown in FIG. 13 at the step 1210 for Example 1 is feedstock cannabinoid material, Δ9-tetrahydrocannabinol ("THC"). One major peak eluted at 10.486 min. suggesting that the sample is predominantly Δ9-tetrahydrocannabinol (THC), while minor peaks suggest the presence of other cannabinoids such as cannabidiol ("CBD") and cannabichromene ("CBC").

Figure 14:
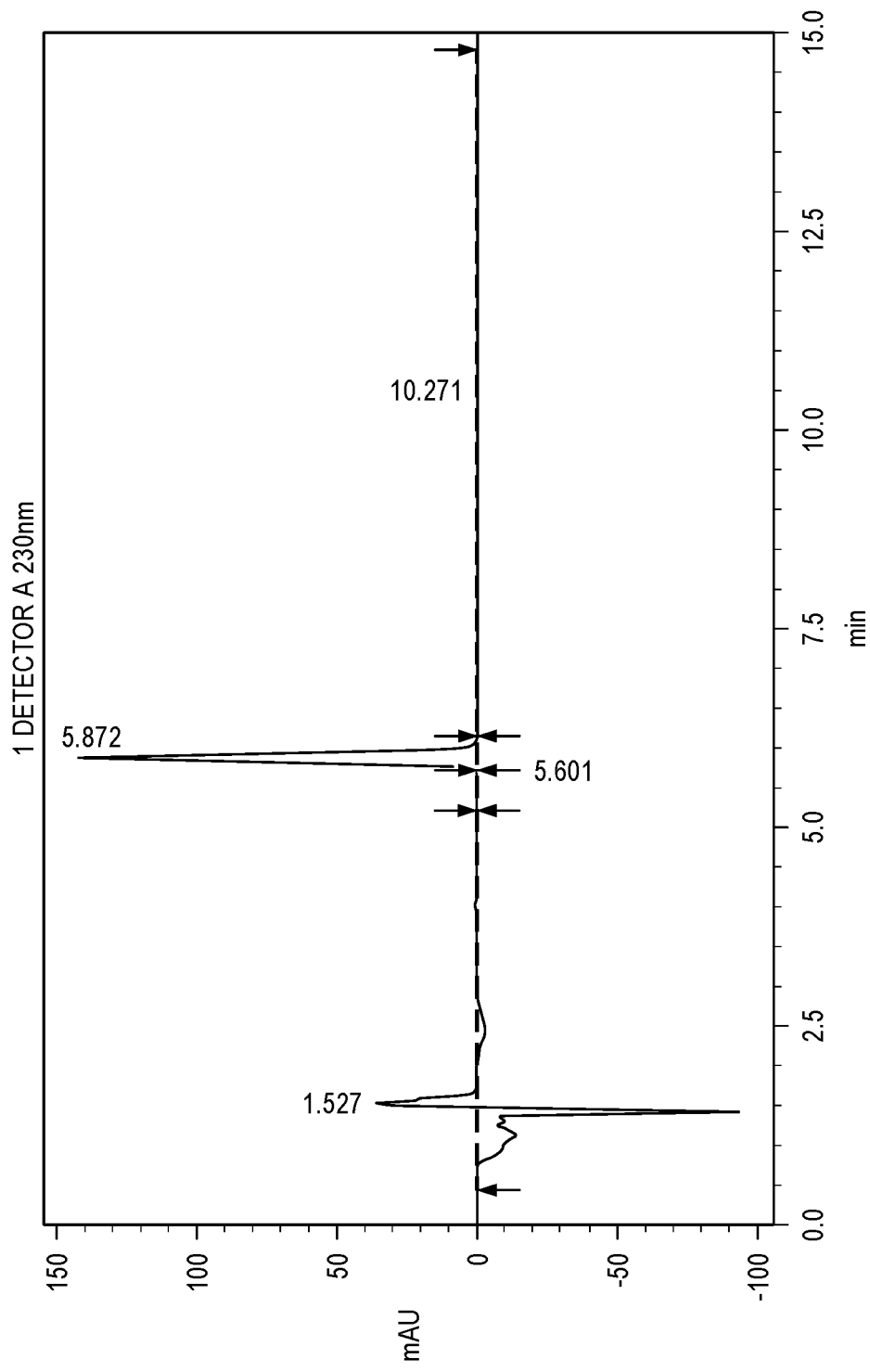
Figure 15:
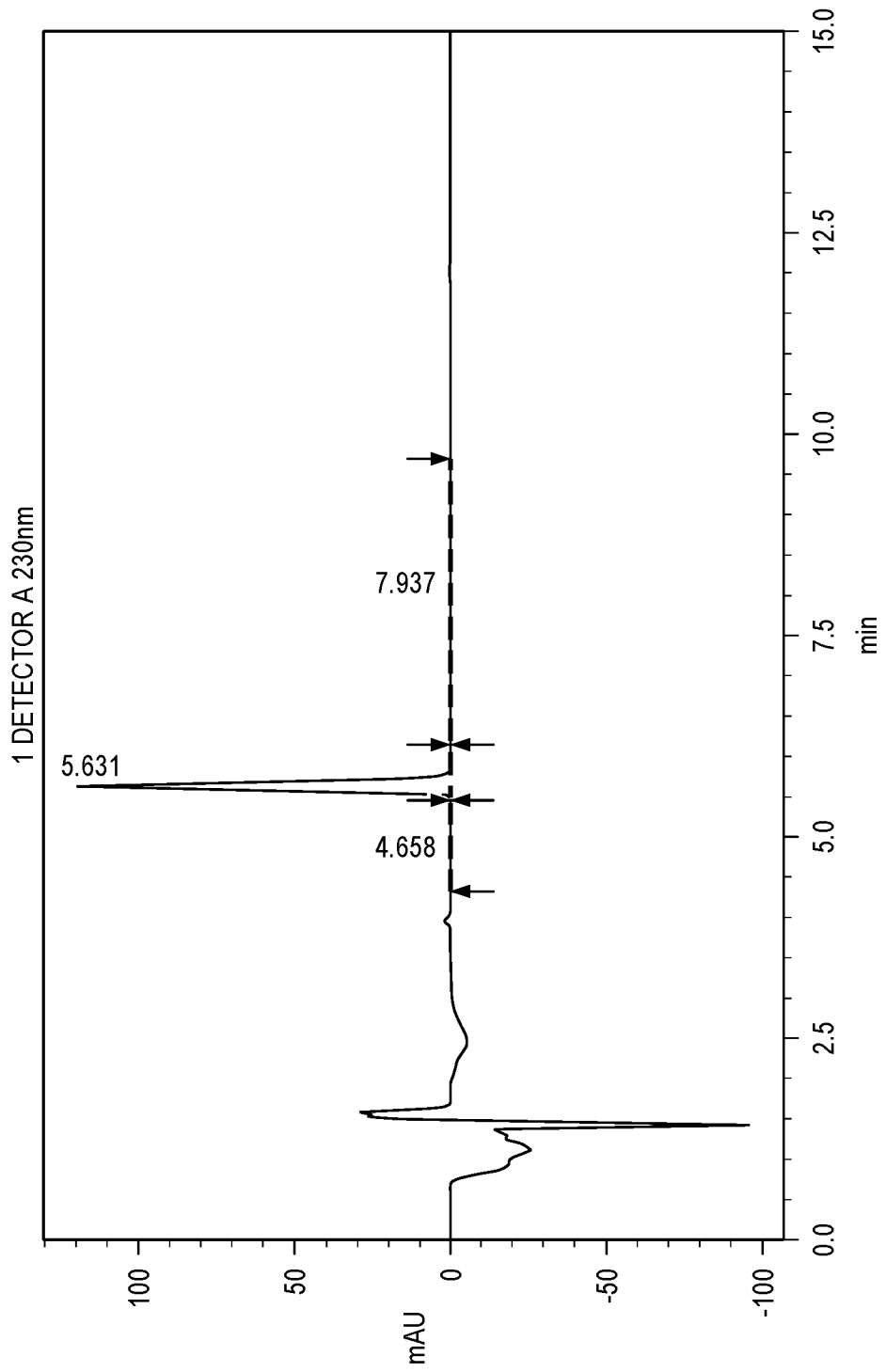
Figure 16:
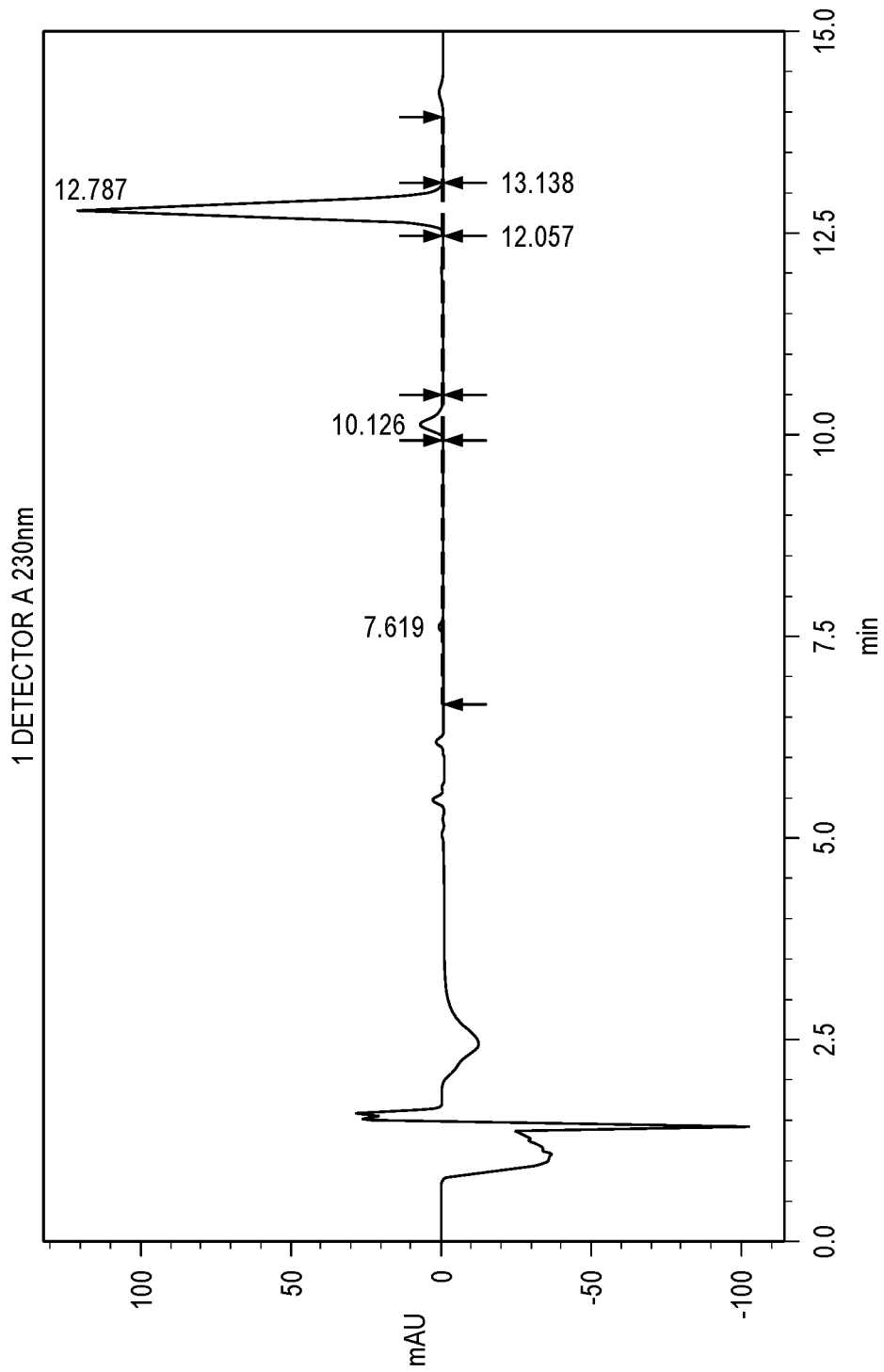
Figure 17:
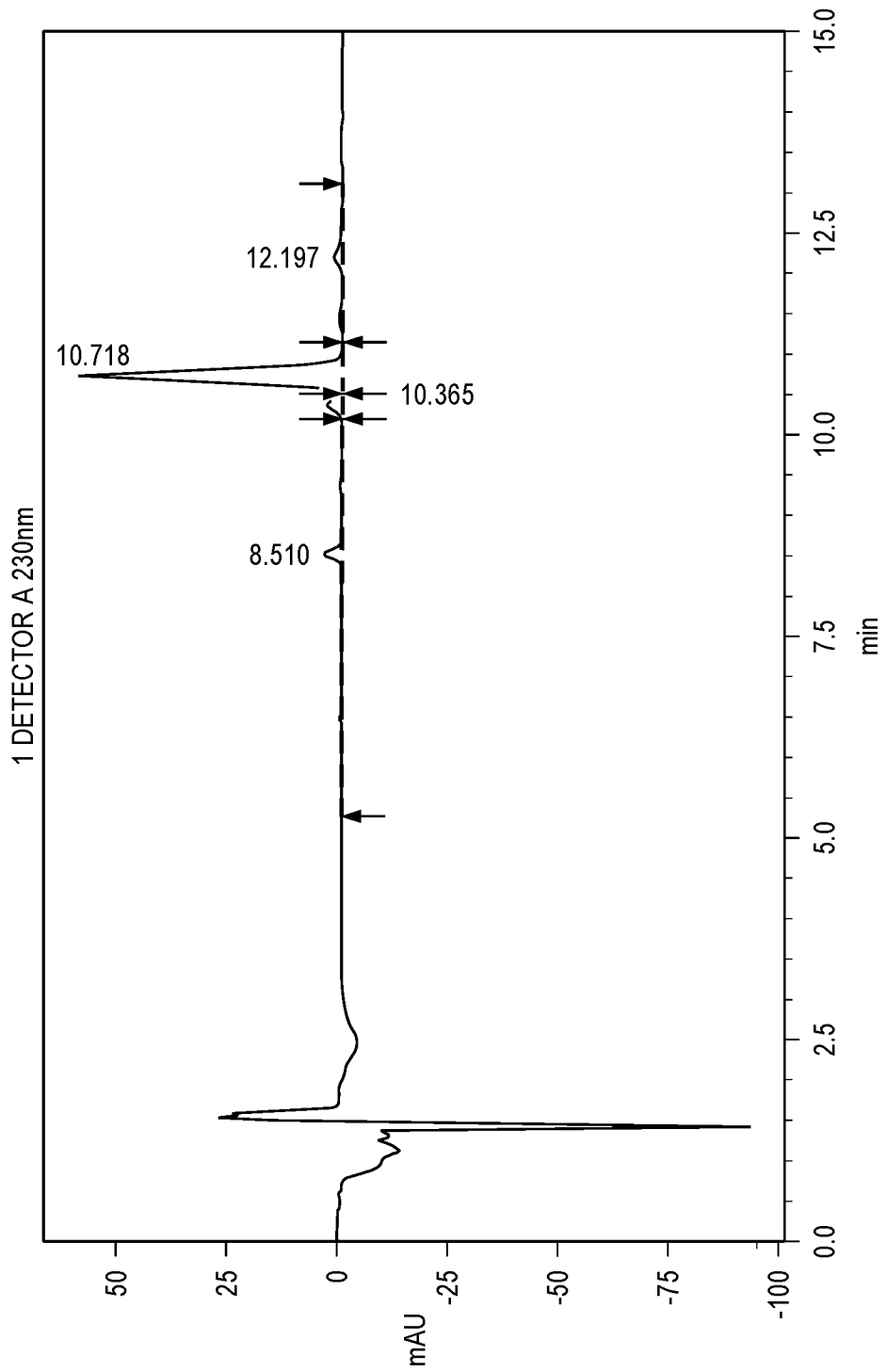

The chromatogram shown in FIG. 14 at the step 1210 for Example 1 is feedstock cannabinoid material, cannabidiol ("CBD"). One major peak eluted at 5.872 min. suggesting that the sample is predominantly cannabidiol ("CBD"), while a lack of minor peaks indicates no presence of other cannabinoids. The chromatogram shown in FIG. 15 at the step 1210 for Example 1 is feedstock cannabinoid material, cannabigerol ("CBG"). One major peak eluted at 5.631 min. suggesting that the sample is predominantly CBG, while one minor peaks indicates the presence of another cannabinoid The chromatogram shown in FIG. 16 at the step 1210 for Example 1 is feedstock cannabinoid material, Δ9-tetrahydrocannabinolic acid ("THCA"). One major peak eluted at 12.787 min. suggesting that the sample is predominantly Δ9-tetrahydrocannabinolic acid ("THCA"), while minor peaks indicates the presence of other cannabinoids such as Δ9-tetrahydrocannabinol ("THC"). The chromatogram shown in FIG. 17 at the step 1210 for Example 1 is feedstock cannabinoid material, Δ8-tetrahydrocannabinol. One major peak eluted at 10.718 min. suggesting that the sample is predominantly Δ8-tetrahydrocannabinol, while minor peaks indicates the presence of other cannabinoids such as Δ9-tetrahydrocannabinol and cannabinol.

The chromatogram shown in FIG. 18 at the step 1250 for Example 2 is of cannabinoid-loaded silica (CLS-1). One major peak eluted at 10.509 min. suggesting that the sample is predominantly Δ9-tetrahydrocannabinol ("THC"), while minor peaks indicates the presence of other cannabinoids such as cannabidiol ("CBD") and cannabichromene ("CBC"). The chromatogram shown in FIG. 19 at the step 1250 for Examples 3 and 6 is of cannabinoid-loaded silica-2 (CLS-2). One major peak eluted at 5.995 min. suggesting that the sample is predominantly cannabidiol ("CBD"), while a lack of minor peaks indicates no presence of other cannabinoids.

Figure 20:
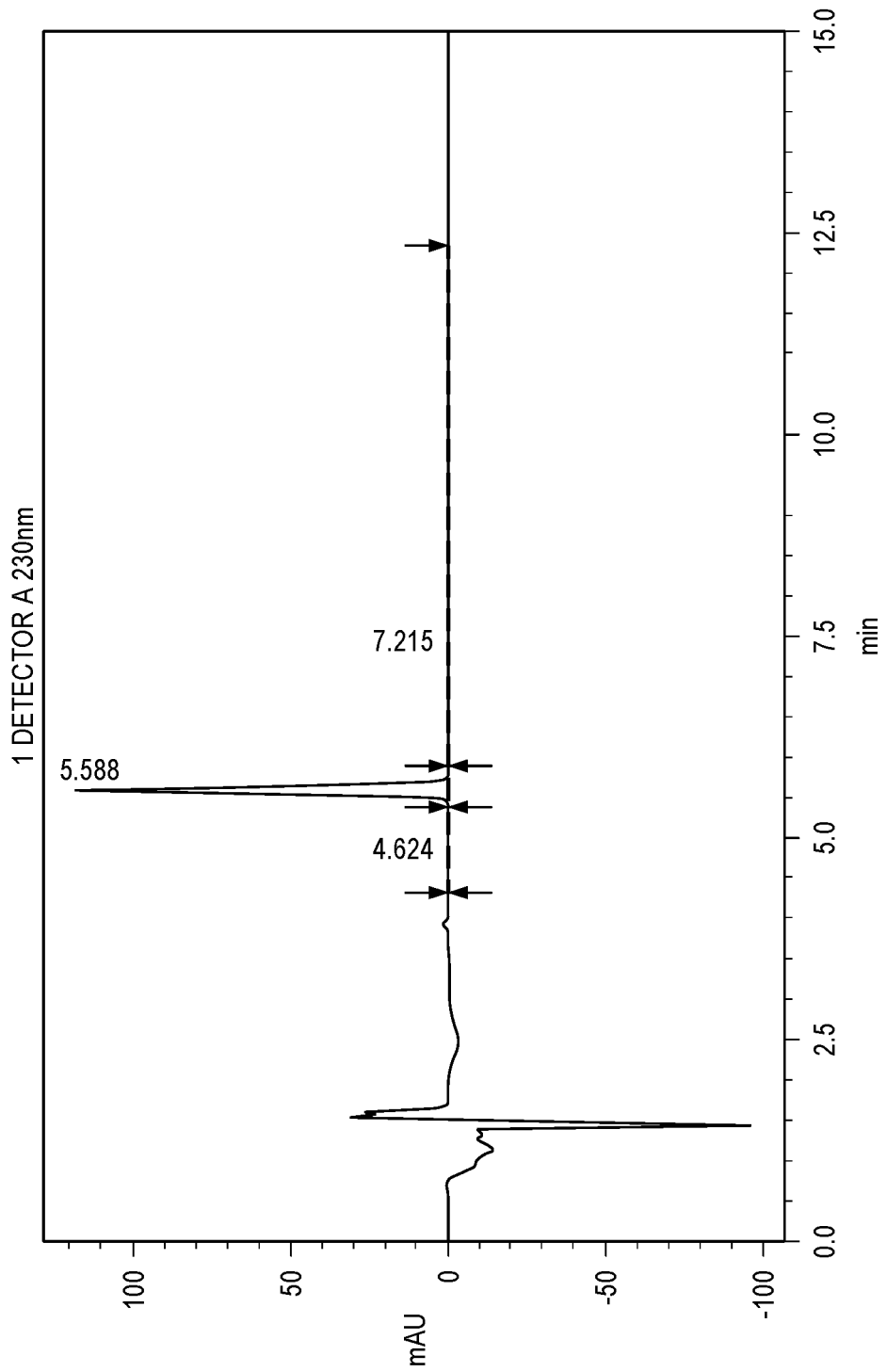
Figure 21:
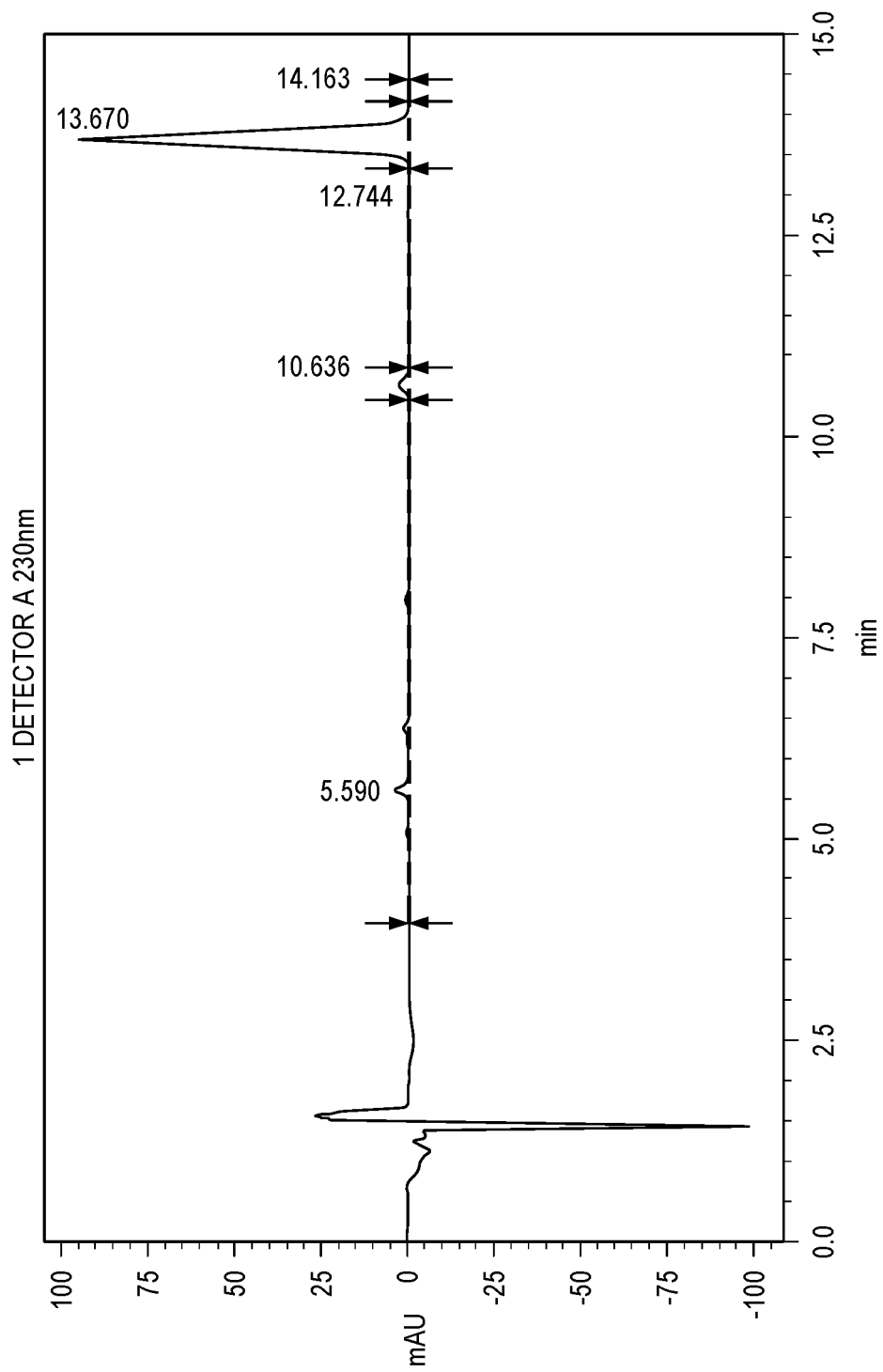

The chromatogram shown in FIG. 20 at the step 1250 for Example 6 is of cannabinoid-loaded silica-2 (CLS-2). One major peak eluted at 5.588 min. suggesting that the sample is predominantly cannabigerol ("CBG"), while a lack of minor peaks suggest no presence of other cannabinoids. The chromatogram shown in FIG. 21 at the step 1250 for Example 6 is of cannabinoid-loaded silica-2 (CLS-2). One major peak eluted at 13.670 min, suggesting that the sample is predominantly Δ9-tetrahydrocannabinolic acid ("THCA"), while minor peaks suggest the presence of other cannabinoids such as Δ9-tetrahydrocannabinol ("THC").

Figure 22:
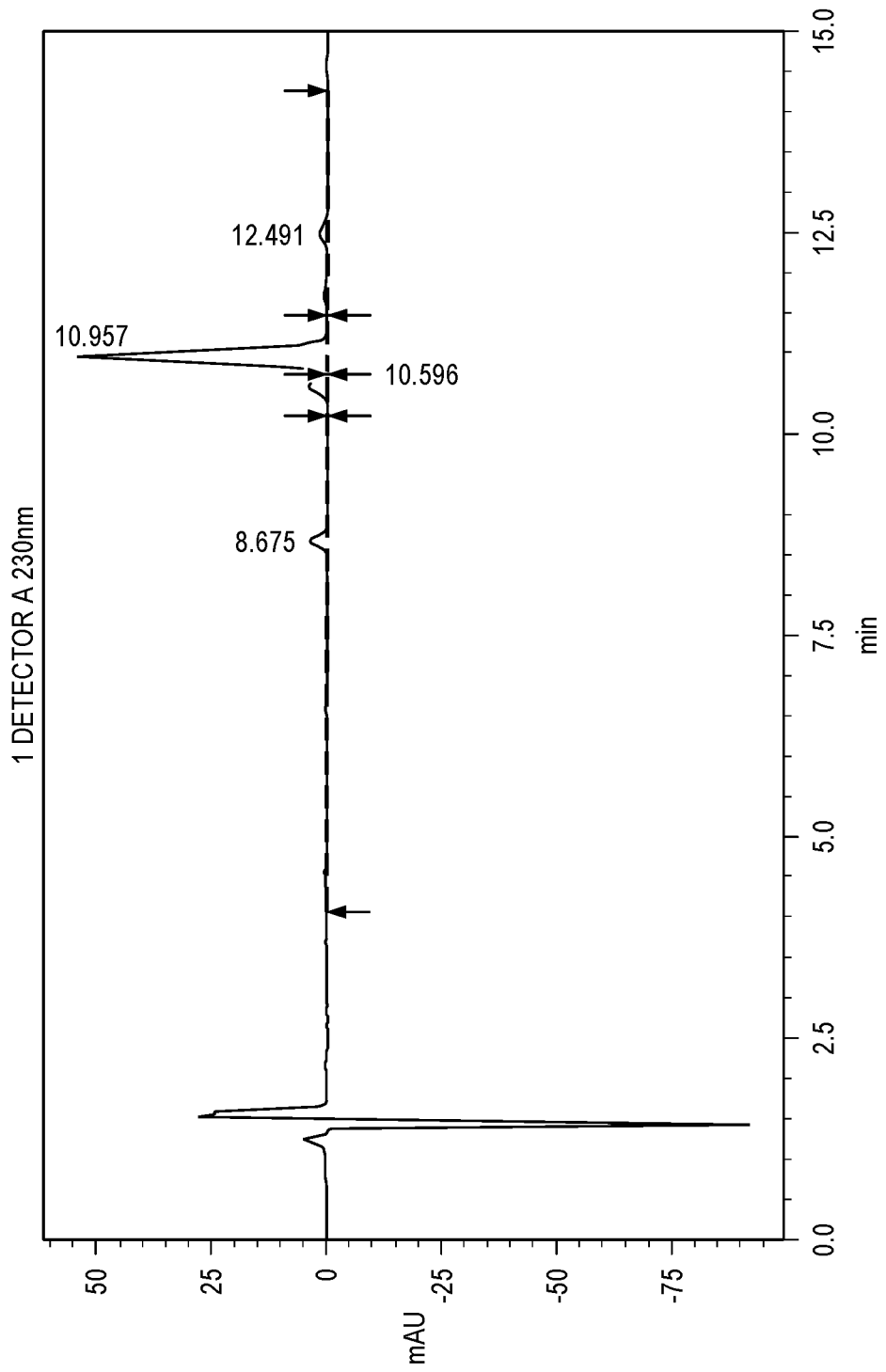

The chromatogram shown in FIG. 22 at the step 1250 for Example 6 is of cannabinoid-loaded silica-1 (CLS-1). One major peak eluted at 10.957 min. suggesting that the sample is predominantly Δ8-tetrahydrocannabinol (Δ8-THC), while minor peaks suggest the presence of other cannabinoids such as cannabinol ("CBD") and Δ9-tetrahydrocannabinol ("THC"). The chromatogram shown in FIG. 23 at the step 1270 for Example 4 is of total formulated powder ("TFP") to be compressed into tablets. One major peak eluted at 10.540 min. suggesting that the sample is predominantly Δ9-tetrahydrocannabinol ("THC"), while minor peaks suggest the presence of other cannabinoids such as cannabidiol ("CBD"), cannabinol ("CBN"), and cannabichromene ("CBC").

The chromatogram shown in FIG. 24 at the step 1270 for Example 5 is of total formulated powder ("TFP") to be compressed into tablets. One major peak eluted at 5.987 min. suggesting that the sample is predominantly cannabidiol ("CBD"), while a lack of minor peaks suggest no presence of other cannabinoids. The chromatogram shown in FIG. 25 at the step 1270 for Example 6 is of total formulated powder ("TFP") to be compressed into tablets. Four major peak eluted at 5.641, 5.901, 10.756, 13.285 min. suggest that the sample is predominantly cannabigerol ("CBG"), cannabidiol ("CBD"), Δ8-tetrahydrocannabinol (Δ8-THC), and Δ9-tetrahydrocannabinolic acid ("THCA"), respectively; while minor peaks suggest the presence of other cannabinoids such as Δ9-tetrahydrocannabinol ("THC").

Figure 26:
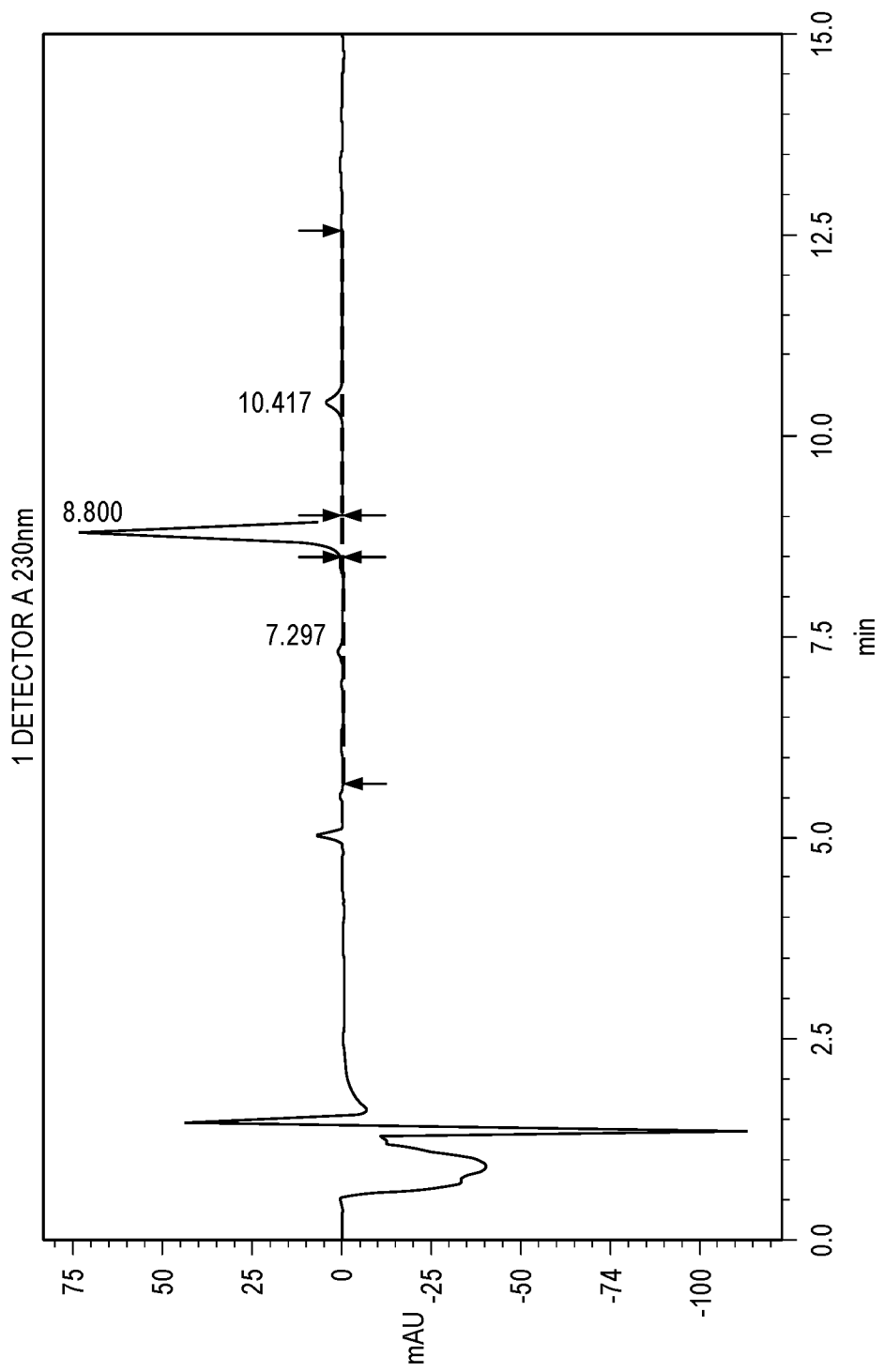
Figure 27:
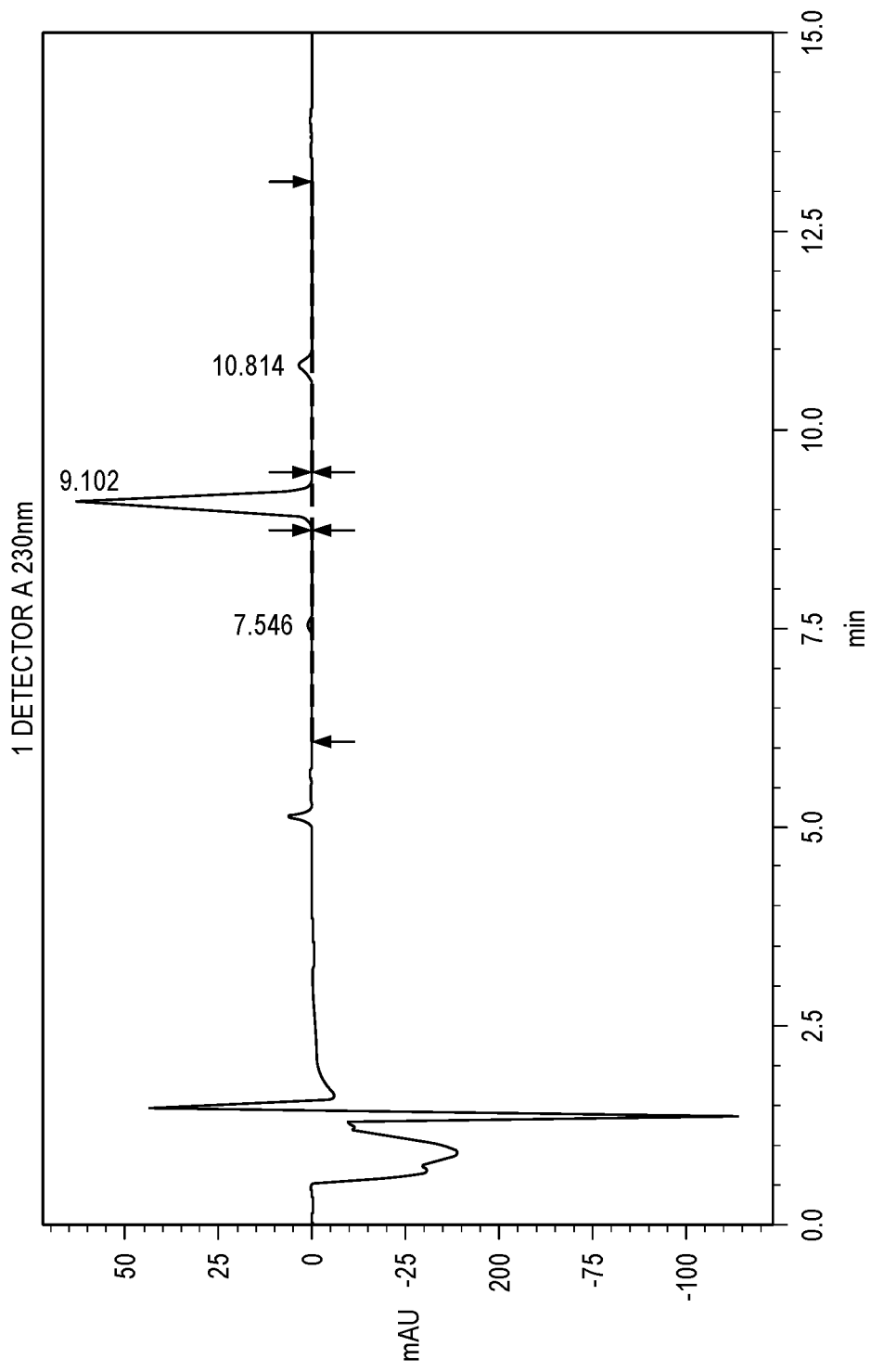
Figure 28:
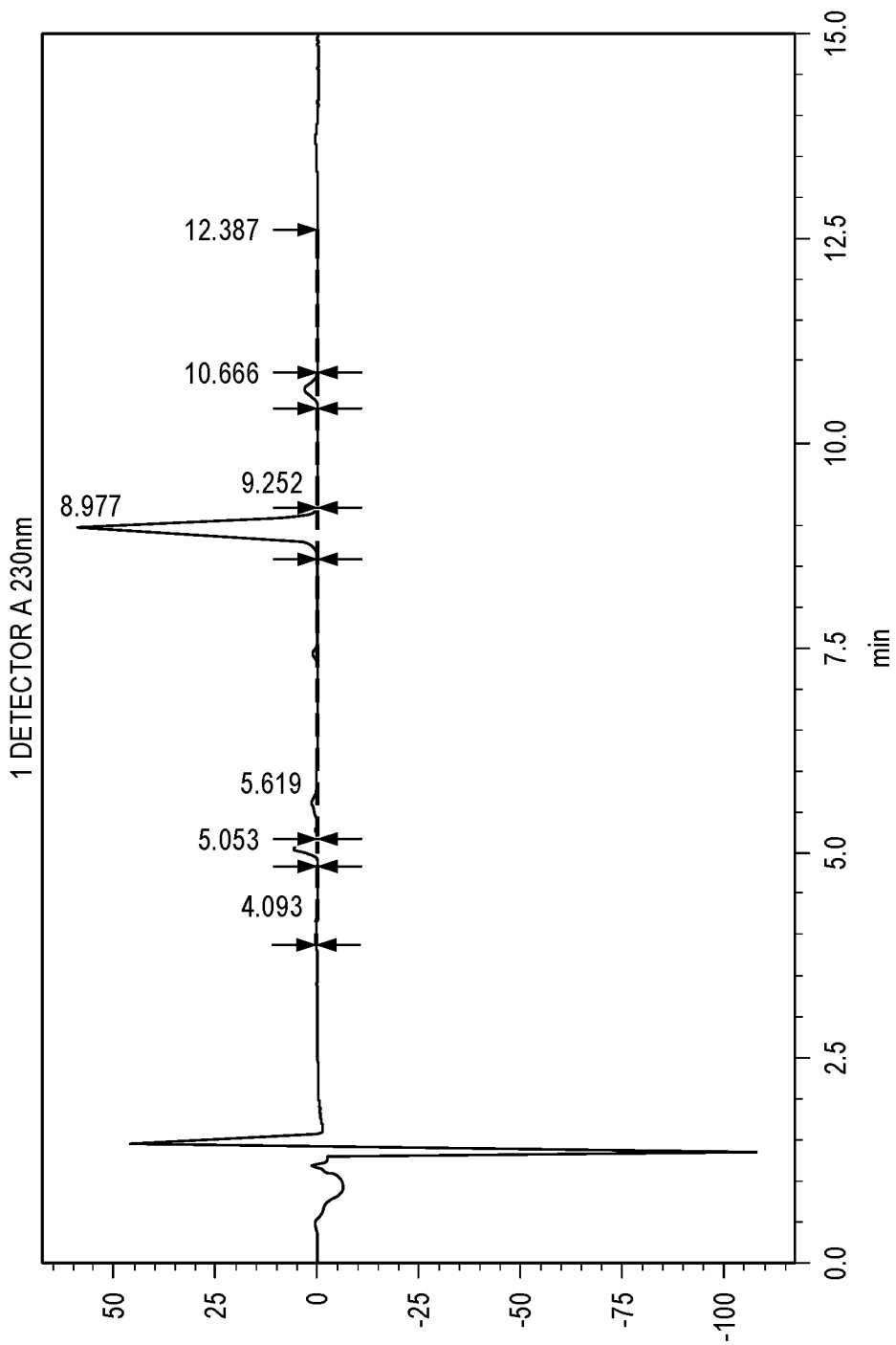

The following provides further examples in accordance with FIGS. 26 to 28.

EXAMPLE 7

A cannabinoid-containing silica (CLS-3) without surfactant is prepared via high-shear blending. The composition of CLS using an amorphous resinous cannabinoid containing ballast (naturally occurring lipids, starches, and waxes) from the originating plant material is described in Table 8.

TABLE 8

| Composition of CLS-3 | |
|---|---|
| Component | wt. % |
| Amorphous Cannabinoid | 46.7 |
| Silicon dioxide | 53.3 |

A granulation containing an appropriate purity threshold of amorphous cannabinoid and silicon dioxide is combined at 42.4 percent cannabinoid loading concentration. Amorphous cannabinoid (e.g., Δ9-tetrahydrocannabinol, FIG. 26) is heated in the oven [at 80 to 120° C.] until desired viscosity is achieved. Cannabinoid is transferred to appropriate vessel and covered to prevent addition of adventitious water. The vessels are cooled [at −40 to −80° C.] for 0 to 1 hours. The amount of cannabinoid is measured, combined with pre-measured mass of silica, and mixed until completely homogenous. Homogeneity is achieved in 90 seconds to 270 seconds (depending on cannabinoid). When homogeneity is achieved, all materials are removed and transferred to a 600 μm ultrasonic and vibratory sieve. The ballast cannabinoid loaded silica-3 (bCLS-3) potency is analyzed using HPLC (FIG. 27).

EXAMPLE 8

An amorphous resinous cannabinoid-loaded silica obtained in Example 7 is blended with excipients and directly compressed into tablets including 25 mg of active cannabinoid for oral administration. The composition of the powder and compressed tablet is described in Table 9.

TABLE 9

| Composition of formulated powder | |
|---|---|
| Component | wt. % |
| bCLS-3 (sans surfactant) | 45.7 |
| Microcrystalline Cellulose | 48.0 |
| Croscarmellose Sodium | 5.0 |
| Magnesium Stearate | 1.0 |
| Terpenoid | 0.3 |

The compressed tablets have an average weight of 175 mg and composed of 45.7 wt. % of CLS-3, 48.0 wt. % of microcrystalline cellulose, 5.0 wt. % of croscarmellose sodium, 1.0 wt. % of lubricant, and 0.3 wt. % terpenoid mixture. The tablets are quality-controlled for specifications (described in Table 7 above) and stored in appropriate containers. The total formulated powder ("TFP") cannabinoid potency is analyzed using HPLC (FIG. 28).

The chromatogram shown in FIG. 26 at the step 1210 for Example 7 is ballast containing feedstock cannabinoid material, Δ9-tetrahydrocannabinol ("THC"). One major peak eluted at 8.800 min. suggesting that the sample is predominantly Δ9-tetrahydrocannabinol (THC). The chromatogram shown in FIG. 27 at the step 1240 for Example 7 is of ballast-cannabinoid-loaded silica-3 (bCLS-3). One major peak eluted at 9.102 min. suggesting that the sample is predominantly Δ9-tetrahydrocannabinol (Δ9-THC). The chromatogram shown in FIG. 28 at the step 1270 for Example 7 is of total formulated powder ("TFP") to be compressed into tablets. One major peak eluted at 8.977 min. suggesting that the sample is predominantly Δ9-tetrahydrocannabinol ("THC").

Thus, an activated cannabinoid controlled release compound tablet and methods of forming the same have been introduced herein. The result is a tablet with a known quantity of a cannabinoid active pharmaceutical ingredient that can be easily consumed by a user, with a predictable pharmaceutical result, and that retains its pharmacological properties over a period of time.

In one embodiment with continuing reference to the previously introduced FIGUREs, the tablet (110) includes a cannabinoid (210) and a hosting compound (220) mixed with the cannabinoid (210) to form a cannabinoid controlled release compound (230). The hosting compound (220) may be mixed with the cannabinoid (210) by blending the hosting compound (220) with the cannabinoid (210) at 1,000 to 30,000 revolutions per minute for 1-30 minutes. The hosting compound (220) may include mesoporous silica, amorphous silica nanoparticles ("ASN"), ceramic nanoparticles ("CNP"), polymeric micelles, drug encapsulated polymeric nanoparticles, lipid polymer hybrid nanoparticles, lipid based nanoparticles, solid lipid nanoparticles ("SLN") and/or mesoporous alumina. The cannabinoid (210) may be heated and cooled prior to mixing the hosting compound (220) with the cannabinoid (210). The cannabinoid (210) may be heated to a temperature of 95 to 100 degrees Celsius for 45 to 60 minutes and the cannabinoid (210) is cooled to a temperature less than minus ten degrees Celsius for 10 to 16 minutes.

The tablet (110) may also include a surfactant (240) mixed with the cannabinoid controlled release compound (230) to form an activated cannabinoid controlled release compound (250). The surfactant (240) may include anionic surfactants such as sodium lauryl sulfate ("SLS"), sodium lauryl ethyl sulfate ("SLES") and/or ammonium lauryl sulfate ("ALS"). The surfactant (240) may include cationic surfactants such as methyl triethanolammonium ("MTEA"). The surfactant (240) may include polymeric surfactants such as polyEO-PolyPO block copolymers and/or alkyl glycosides.

The tablet (110) may also include sodium croscarmellose (1130), microcrystalline cellulose ("MCC") (1140) and/or a lubricant (1150) mixed with the activated cannabinoid controlled release compound (250). The lubricant (1150) may include magnesium stearate and/or hydroxymethyl cellulose.

The tablet (110) may also include a terpenoid (810) added to and homogenized with the activated cannabinoid controlled release compound (250) to form a dry powder (850). The dry powder (850) of the activated cannabinoid controlled release compound (250) is compressed to form the tablet (110). The terpenoid (810) may include monoterpenoid, sesquiterpenoid, diterpenoid and/or triterpenoid. The monoterpenoid may include alpha-pinene and/or linalool. The sesquiterpenoid may include farnesene and/or nerolidol. The diterpenoid may include cembrene A and/or phytol. The triterpenoid may include squalene.

Although the embodiments and its advantages have been described in detail, it should be understood that various changes, substitutions, and alterations can be made herein without departing from the spirit and scope thereof as defined by the appended claims. Many of the features, functions, and steps of forming the same may be reordered, omitted, added, etc., and still fall within the broad scope of the various embodiments.

Moreover, the scope of the various embodiments is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized as well. Accordingly, the appended claims are intended to include within their scope such processes, machines, manufacture, compositions of matter, means, methods, or steps.

What is claimed is:

1. A tablet, consisting of:
   a cannabinoid in a solid form;
   mesoporous silica in a solid form mixed with said cannabinoid to form a dry powdery activated cannabinoid controlled release compound;
   sodium croscarmellose, microcrystalline cellulose (MCC) and a lubricant mixed with said activated cannabinoid controlled release compound; and
   a terpenoid added to and homogenized with said activated cannabinoid controlled release compound.

2. The tablet as recited in claim 1 wherein said cannabinoid is heated and cooled prior to said mixing said mesoporous silica with said cannabinoid.

3. The tablet as recited in claim 2 wherein said cannabinoid is heated to a temperature of 95 to 100 degrees Celsius for 45 to 60 minutes and said cannabinoid is cooled to a temperature less than minus ten degrees Celsius for 10 to 16 minutes.

4. The tablet as recited in claim 1 wherein said mesoporous silica is mixed with said cannabinoid by blending said mesoporous silica with said cannabinoid at 1,000 to 30,000 revolutions per minute for 1-30 minutes.

5. The tablet as recited in claim 1 wherein said lubricant is selected from the group consisting of:
   magnesium stearate; and
   hydroxymethyl cellulose.

6. The tablet as recited in claim 1 wherein said terpenoid is selected from the group consisting of:
   monoterpenoid;
   sesquiterpenoid;
   diterpenoid; and
   triterpenoid.

7. The tablet as recited in claim 6 wherein said monoterpenoid is selected from the group consisting of:
   alpha-pinene; and
   linalool.

8. The tablet as recited in claim 6 wherein said sesquiterpenoid is selected from the group consisting of:
   farnesene; and
   nerolidol.

9. The tablet as recited in claim 6 wherein said diterpenoid is selected from the group consisting of:
   cembrene A; and
   phytol.

10. The tablet as recited in claim 6 wherein said triterpenoid comprises squalene.

11. The tablet as recited in claim 1 wherein said activated cannabinoid controlled release compound is compressed to form said tablet.

12. The tablet as recited in claim 1 wherein said cannabinoid is loaded into pores of said mesoporous silica to facilitate a controlled release character of said activated cannabinoid controlled release compound.

* * * * *